United States Patent [19]

Keck et al.

[11] E Re. 29,628

[45] Reissued May 9, 1978

[54] AMINOBENZYL-AMINES AND SALTS THEREOF

[75] Inventors: Johannes Keck, Biberach an der Riss; Klaus-Reinhold Noll, Warthausen-Oberhofen; Helmut Pieper, Biberach an der Riss; Gerd Kruger, Biberach an der Riss; Sigfrid Puschmann, Biberach an der Riss, all of Germany

[73] Assignee: Boehringer Ingelheim GmbH, Ingelheim am Rhein, Germany

[21] Appl. No.: 746,954

[22] Filed: Dec. 2, 1976

Related U.S. Patent Documents

Reissue of:

[64] Patent No.: 3,950,393
Issued: Apr. 13, 1976
Appl. No.: 458,099
Filed: Apr. 5, 1974

[30] Foreign Application Priority Data

Apr. 13, 1973 Germany ..... 2318636
Jan. 23, 1974 Germany ..... 2402989

[51] Int. Cl.[2] ..... C07C 101/68

[52] U.S. Cl. ..... 560/37; 260/239 B; 260/239 AF; 260/243.3; 260/293.63; 260/293.64; 260/293.77; 260/293.79; 260/326.37; 260/326.4; 260/326.5 L; 260/326.85; 260/465 D; 260/455 E; 260/518 R; 260/518 A; 260/519; 260/558 R; 260/558 A; 260/562 R; 260-562 A; 260/570.9; 424/244; 424/248; 424/248.53; 424/250; 424/248.54; 424/267; 424/274; 424/304; 424/248.55; 424/310; 424/324; 424/330; 424/248.56; 544/86; 544/162; 544/168; 544/372; 544/360; 560/42; 544/399; 544/400; 544/401; 544/398; 544/402

[58] Field of Search ..... 260/471 R, 518 R, 518 A, 260/519; 560/37, 42

[56] References Cited

U.S. PATENT DOCUMENTS 3,793,292 2/1974 Yamamura et al. ..... 260/471 R

OTHER PUBLICATIONS

Felder et al., Helv. Chim. Acta., 48, (1965), pp. 259–274.

*Primary Examiner*—Richard L. Raymond
*Attorney, Agent, or Firm*—Hammond & Littell

[57] ABSTRACT

Compounds of the formula

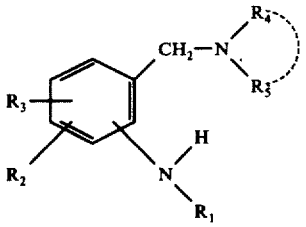

wherein $R_1$ is hydrogen or aliphatic or aromatic carboxylic acyl, $R_2$ is hydrogen, chlorine or bromine, $R_3$ is fluorine, alkyl of 1 to 4 carbon atoms, trifluoromethyl, cyano, carbamoyl, carboxyl, carbalkoxy, alkoxy, acetyl, 1-hydroxyethyl or

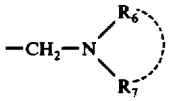

where $R_6$ and $R_7$ are each alkyl, cycloalkyl, hydroxycycloalkyl or, together with each other and the nitrogen atoms to which they are attached, pyrrolidino, piperidino or morpholino, and $R_4$ and $R_5$ are each hydrogen, alkyl of 1 to 5 carbon atoms, mono- or di-hydroxy (alkyl of 1 to 5 carbon atoms), alkenyl of 2 to 4 carbon atoms, cycloalkyl of 5 to 7 carbon atoms, mono- or di-hydroxy(cycloalkyl of 5 to 7 carbon atoms), benzyl, morpholinocarbonylmethyl or, together with each other and the nitrogen atom to which they are attached, pyrrolidino, piperidino, hexamethyleneimino, morpholino, N-methyl-piperazino or camphidino, and non-toxic, pharmacologically acceptable acid addition salts thereof; the compounds as well as their salts are useful as antiulcerogenics, secretolytics, [*antitussive,*] *antitussives* and stimulants of the production of the surfactant or antiatelectasis factor of the alveoli.

5 Claims, No Drawings

AMINOBENZYL-AMINES AND SALTS THEREOF

Matter enclosed in heavy brackets [ ] appears in the original patent but forms no part of this reissue specification; matter printed in italics indicates the additions made by reissue.

This invention relates to novel aminobenzyl-amines and non-toxic acid addition salts thereof, as well as to methods of preparing these compounds.

More particularly, the present invention relates to a novel class of benzylamines represented by the formula

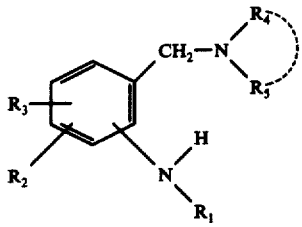

(I)

wherein $R_1$ is hydrogen or aliphatic or aromatic carboxylic acyl, $R_2$ is hydrogen, chlorine or bromine, $R_3$ is fluorine, alkyl of 1 to 4 carbon atoms, trifluoromethyl, cyano, carbamoyl, carboxyl, lower carbalkoxy, lower alkoxy, acetyl, 1-hydroxyethyl or

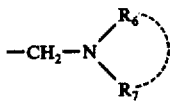

where $R_6$ and $R_7$ are each lower alkyl, cycloalkyl of 5 to 7 carbon atoms, hydroxy-(cycloalkyl of 5 to 7 carbon atoms) or, together with each other and the nitrogen atom to which they are attached, pyrrolidino, piperidino or morpholino, and $R_4$ and $R_5$ are each hydrogen, alkyl of 1 to 5 carbon atoms, mono- or di-hydroxy (alkyl of 1 to 5 carbon atoms), alkenyl of 2 to 4 carbon atoms, cycloalkyl of 5 to 7 carbon atoms, mono- or di-hydroxy(cycloalkyl of 5 to 7 carbon atoms), benzyl, morpholinocarbonylmethyl or, together with each other and the nitrogen atom to which they are attached, pyrrolidino, piperidino, hexamethyleneimino, morpholino, N-methyl-piperazino or camphidino, and nontoxic, pharmacologically acceptable acid addition salts thereof.

The compounds embraced by formula I may be prepared by various methods involving well known chemical synthesis principles, among which the following have proved to be most convenient and efficient:

Method A

By reacting a compound of the formula

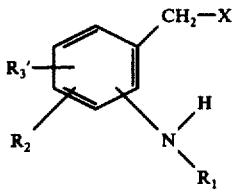

(II)

wherein $R_1$ and $R_2$ have the same meanings as in formula I,

X is chlorine, bromine, iodine, hydroxyl, acyloxy, sulfonyloxy, alkoxy, aryloxy, aralkoxy, trialkylammonium or pyridinium, and $R_3'$ had the meanings defined for $R_3$ in formula I or $—CH_2—X$, where X has the meanings defined above,

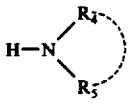

(III)

wherein $R_4$ and $R_5$ have the same meanings as in formula I.

Particularly preferred embodiments of substituent X in formula II are chlorine, bromine, hydroxyl, acetoxy, butyryloxy, benzoyloxy, methylsulfonyloxy, p-toluenesulfonyloxy, methoxy, ethoxy, phenoxy, trimethylammonium and pyridinium. Thus, X may be any group which, starting from a compound of the formula II, easily severs from the molecule and enables the intermediate formation of a benzyl cation.

The reaction is advantageously performed in a solvent medium, such a carbon tetrachloride, chloroform, methanol, tetrahydrofuran, benzene, toluene, ether, dioxane, tetrahydronaphthalene or an excess of the amine of the formula III, and, depending upon the reactivity of substituent X, at temperatures between −70 and +200° C. However, the reaction will also proceed without the presence of a solvent medium.

In those instances where the reaction is performed with a compound of the formula II wherein X is hydroxyl and the 2-position of the phenyl ring is occupied by an acylamino substituent, the acyl moiety of this substituent can be split off during the reaction.

If X in formula II is arylsulfonyloxy, such as p-toluene-sulfonyloxy, the reaction is preferably performed at a temperature between −70 and +50° C in a solvent medium, such as an aliphatic or cyclic ether.

If X in formula II is halogen, the reaction is preferably performed at temperatures between 0 and 150° C, especially at the boiling point of the particular solvent medium which is employed, and advantageously in the presence of a hydrogen halide-binding agent, such as an inorganic base, especially sodium carbonate or sodium hydroxide; an ion exchanger; a tertiary organic base, especially triethylamine or pyridine; or an excess of the particular amine of the formula III. In this case, if a tertiary organic base is used as the hydrogen halide-binding agent, it may simultaneously serve as the solvent medium for the reaction.

If X in formula II is acyloxy, such as acetoxy or benzoyloxy, alkoxy, aryloxy or aralkoxy, the reaction is optionally carried out in the presence of an acid catalyst, such as ammonium chloride, acid aluminum oxide or sulfuric acid, and preferably at temperatures between 0 and 200° C.

If X in formula II is hydroxyl, the reaction is optionally carried out in the presence of an acid catalyst, such as sulfuric acid, hydrobromic acid, p-toluene-sulfonic acid or a lower alkanoic acid, such as propionic acid or butyric acid; it may optionally also be performed in the presence of an alkaline catalyst, such as potassium hydroxide magnesium oxide or sodium amide. In either case the preferred reaction temperature range is from 120 to 180° C, and the reaction may be performed in the presence or absence of a solvent medium.

Finally, if X in formula II is trialkylammonium or pyridinium, the reaction is preferably performed in an excess of the particular amine of the formula III which serves as the solvent medium, and at a temperature between 120 and 180° C. However, the reaction also proceeds in the absence of a solvent medium.

Method B

For the preparation of a compound of the formula I wherein $R_2$ is chlorine or bromine, and $R_4$ and/or $R_5$ have the meanings previously defined, except alkenyl of 2 to 4 carbon atoms, by halogenating a compound of the formula

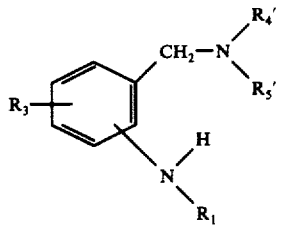

(IV)

wherein $R_1$ and $R_3$ have the same meanings as in formula I, and $R_4'$ and $R_5'$ have the same meanings as $R_4$ and $R_5$ in formula I, except alkenyl of 2 to 4 carbon atoms.

The halogenation is effected with a conventional halogenating agent, such as chlorine, bromine, bromo tribromophenate or phenyl iodide dichloride, preferably in a solvent medium, such as 50–100% acetic acid, methylene chloride or tetrahydrofuran, in the presence of a tertiary organic base, such as triethylamine or pyridine, and advantageously at a temperature between −20 and +50° C. 1 mol of halogenating agent or a slight excess thereover is provided per mol of compound IV; the latter may be employed in the form of its free base or also in the form of an acid addition salt, such as its mono-, di- or trihydrochloride. If the end product obtained by this method is a hydrohalic acid addition salt of a compound of the formula I, the same may by isolated as such or further purified by way of its free base.

Method C

For the preparation of a compound of the formula I wherein $R_1$ and/or $R_4$ are hydrogen, by splitting off one or two protective groups from a compound of the formula

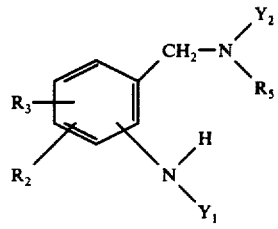

(V)

wherein $R_2$, $R_3$ and $R_5$ have the same meanings as in formula I, $Y_1$ has the meanings defined above for $R_1$ or is an amino-protective group which can be split off by hydrolysis or hydrogenation, and $Y_2$ has the meanings defined above for $R_4$ or is an amino-protective group which can be split off by hydrolysis or hydrogenation, provided, however, that at least one of $Y_1$ and $Y_2$ must be an amino-protective group.

For instance, if $Y_1$ and/or $Y_2$ are acyl, such as acetyl, benzoyl or p-toluenesulfonyl, trimethylsilyl or tetrahydropyranyl-(2), the removal of these protective group is effected by hydrolysis in the presence of a solvent, such as with ethanolic hydrochloric acid or aqueous-ethanolic sodium hydroxide, at temperatures between 20 and 150° C, but preferably at the boiling point of the particular solvent which is used. If $R_3$ in formula V is cyano, carbalkoxy or carbamoyl, these substituents can be simultaneously hydrolized into carboxyl by this method.

On the other hand, if $Y_1$ and/or $Y_2$ are benzyloxycarbonyl or benzyl, for example, the removal of these protective groups is effected by hydrogenation, such as with hydrogen in the presence of palladium as a catalyst, for example, and preferably at room temperature in the presence of a solvent, such as methanol, methanol/water or methanol/hydrochloric acid. If $R_4$ and/or $R_5$ in formula V are alkenyl of 2 to 4 carbon atoms, these are simultaneously reduced to alkyl; likewise, if $R_3$ in formula V is acetyl or cyano, these substituents are simultaneously reduced.

Method D

For the preparation of a compound of the formula I wherein $R_3$ is 1-hydroxy-ethyl, by reducing a compound of the formula

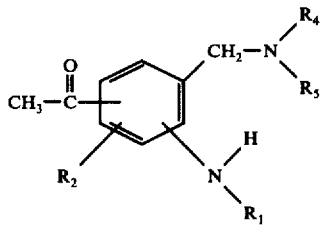

(VI)

wherein $R_1$, $R_2$, $R_4$ and $R_5$ have the same meanings as in formula I.

The reduction is preferably carried out in a solvent medium, such as methanol, methanol/water, ethanol, isopropanol, ether, tetrahydrofuran or dioxane, at a temperature between −20° C and the boiling point of the particular solvent which is used.

The reduction may be effected with a complex metal hydride, such as lithium aluminum hydride or especially sodium borohydride; or with an aluminum alcoholate, such as aluminum isopropylate, in the presence of a primary or secondary alkanol, such as ethanol or isopropanol; or with hydrogen in the presence of a hydrogenation catalyst, such as Raney nickel, platinum or palladized charcoal.

If the reduction is effected with catalytically activated hydrogen, and $R_4$ and/or $R_5$ in formula VI are alkenyl of 2 to 4 carbon atoms and/or benzyl, the alkenyl substituents are simultaneously reduced to the corresponding alkyl substituents, while the benzyl substituents are split off.

Method E

For the preparation of a compound of the formula I wherein $R_3$ is carboxyl, by hydrolizing a compound of the formula

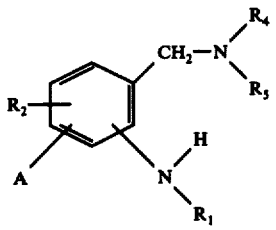

(VII)

wherein $R_1$, $R_2$, $R_4$ and $R_5$ have the same meanings as in formula I, and control A is a functional derivative of carboxyl, such as amido, imido, alkoxycarbonyl or cyano.

The hydrolysis is advantageously performed in a solvent, such as methanol, ethanol, methanol/water, ethanol/water, dioxane/water or water, in the presence of an acid, such as trifluoroacetic acid, hydrochloric acid or sulfuric acid, or in the presence of a base, such as sodium hydroxide, and at temperatures between 50 and 150° C, but preferably at the boiling point of the particular solvent which is used.

If $R_1$ in formula VII is acyl, this substituent is simultaneously split off during the hydrolysis.

Method F

For the preparation of a compound of the formula I wherein $R_1$ is hydrogen, $R_3$ has the meanings previously defined except cyano, carboxyl, carbalkoxy, carbamoyl and acetyl, and $R_4$ and/or $R_5$ have the meanings defined above except morpholinocarbonyl-methyl, by reducing a compound of the formula

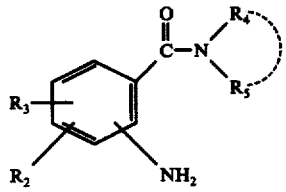

(VIII)

wherein $R_2$ has the same meanings as in formula I, $R_4$ and $R_5$ have the same meanings as in formula I except morpholinocarbonyl-methyl, and $R_3$ has the meanings defined in formula I except cyano, carboxyl, carbamoyl, carbalkoxy and acetyl.

The reduction is advantageously performed in a solvent with nascent hydrogen, such as with sodium in ethanol; or with catalytically activated hydrogen; or with a complex metal hydride, such as with sodium borohydride in pyridine or, most preferably, with lithium aluminum hydride in ether or tetrahydrofuran. The reduction is carried out at moderately elevated temperatures. such as between 30 and 70° C, or at the boiling point of the particular solvent which is used.

In those instances where methods A, B or C yield a compound of the formula I wherein $R_3$ is cyano, this compound may be converted into the corresponding carbamoyl-substituted compound by partial hydrolysis, such as with aqueous-ethanolic sodium hydroxide.

If the above methods yield a compound of the formula I wherein $R_1$ is hydrogen and $R_2$, $R_3$, $R_4$ and $R_5$ have the meanings previously defined except substituents containing a reactive hydrogen atom, such a compound may, if desired, be subsequently acylated. The acylation is advantageously carried out with a reactive derivative of an acid, such as an acid halide, acid anhydride or mixed acid anhydride, or in the presence of a dehydrating agent, such as N,N'-dicyclohexyl-carbodiimide.

The starting compounds for methods A to F are either known compounds and/or may be prepared by known processes.

For example, a compound of the formula II may be obtained by reacting a corresponding toluene derivative with N-bromo-succinimide or with halogen under ultraviolet radiation; or also by reacting a corresponding benzyl alcohol with thionyl chloride; or by reacting a corresponding benzyl halide with an alkali metal salt of a carboxylic acid, an alkali metal alcoholate or alkali metal phenolate; or by halogenating a corresponding benzylammonium salt.

The benzylamines of the formulas IV, V, VI and VII may be obtained by reacting a corresponding halide with a corresponding amine.

The benzamides of the formula VIII may be obtained, for example, by reacting a corresponding isatoic acid anhydride with a corresponding amine.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, fumaric acid, 8-chlorotheophylline or the like.

The following examples further illustrate the present invention and will enable others skilled in the art to understand it more completely. It should be understood, however, that the invention is not limited solely to the particular examples given below.

EXAMPLE 1

2-Amino-3-bromo-N,N-dimethyl-5-fluoro-benzylamine and its hydrochloride by method A 5.5 gm of 2-amino-3-bromo-5-fluoro-benzyl alcohol were dissolved in 150 ml of chloroform. While stirring and cooling the solution with ice, 7.13 gm (4.35 ml) of thionyl) chloride were added dropwise, whereby a yellow precipitate formed. The resulting suspension was allowed to stand overnight, and was then evaporated to dryness in vacuo in a rotary evaporator at room temperature. The crude benzyl chloride thus obtained was suspended in 100 ml of chloroform. While stirring and cooling the suspension with ice, 20 ml of dimethylamine were added, whereby a clear solution was formed, which was allowed to stand for 30 minutes on an ice bath and was then extracted twice with saturated potassium carbonate solution. The chloroform phase was washed with water, dried over sodium sulfate and evaporated to dryness in vacuo. The residue, 2-amino-3-bromo-5-fluoro-N,N-dimethyl-benzyl-amine, was taken up in absolute ethanol, and the solution was acidified with ethereal hydrochloric acid to pH 3. The precipitate formed thereby was vacuum-filtered off and dissolved in absolute ethanol. After addition of charcoal, the solution was heated to the boiling point. After filtering off the charcoal and adding ether, colorless crystals were obtained which were identified to be the hydrochloride of the formula

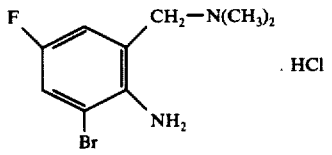

having a melting point of 241–243° C.

EXAMPLE 2

2-Acetylamino-N,N-diethyl-3-methyl-benzylamine and its tartrate by method A 20 gm of diethylamine were added to a solution of 22 gm of 2-acetylamino-3-methyl-benzyl bromide in 1.6 liters of carbon tetrachloride, and the mixture was refluxed for 1 hour. Subsequently, the reaction solution was evaporated, the residue was dissolved in 1 liter of 2 N hydrochloric acid, the solution as extracted twice with chloroform, and the acid phase was made alkaline with concentrated ammonia and extracted three times with chloroform. The organic phase was evaporated, and the residue was chromatographed on silicagel with acetone/methanol (9:1). The crude product thus obtained was dissolved in ethanol, the solution was acidified with ethanolic tartaric acid, and 2-acetylamino-N,N-diethyl-3-methyl-benzylamine was caused to crystallize out as its tartrate, m.p. 134–136° C, by addition of ether.

EXAMPLE 3

2-Acetylamino-5-bromo-N,N-diethyl-3-diethylaminomethyl-benzylamine by method A 24 gm of diethylamine were added to a solution of 16.5 gm of 2-acetylamino-5-bromo-3-bromomethyl-benzyl bromide in 1.6 liters of carbon tetrachloride, and the mixture was refluxed for 1 hour. Subsequently, the reaction solution was evaporated, the residue was dissolved in 0.7 liter of 2 N hydrochloric acid, and the solution was extracted twice with chloroform. The hydrochloric acid phase was made alkaline with concentrated ammonia and extracted three times with chloroform. The organic base was dried with sodium sulfate, and the solvent was distilled off. The residue was purified by column-chromatography on silicagel with ethyl-acetate/methanol (1:1), the corresponding fractions were united, and 2-acetylamino-5-bromo-N,N-diethyl-3-diethylamino-methyl-benzylamine, m.p. 91.5–93° C, was obtained by recrystallization from petroleum ether.

EXAMPLE 4

2-Acetylamino-5-bromo-4-tert.butyl-N-cyclohexyl-N-methyl-benzylamine hydrochloride by method A A mixture of 25 gm of 2-acetylamino-5-bromo-4-tert-.butyl-benzyl bromide, 1.5 liters of carbon tetrachloride and 23 gm of N-methyl-cyclohexylamine was refluxed for 1 hour. After cooling, the precipitated N-methyl-cyclohexylamine hydrobromide was filtered off and the filtrate was evaporated. The residue was admixed with 2 N hydrochloric acid, and the mixture was extracted twice with benzene. The acid phase was made alkaline with concentrated ammonia, extracted three times with chloroform, and the organic phase was dried and evaporated. The residue was purified by column-chromatography on silicagel with ethylacetate/chloroform (1:1), and 2-acetylamino-5-bromo-4-tert.butyl-N-cyclohexyl-N-methyl-benzylamine hydrochloride was precipitated from a solution of the purified residue in ethanol/ether with ethanolic hydrochloric acid. The crude product was recrystallized from ethanol-ether, whereupon it had a melting point of 231–234° C.

EXAMPLE 5

2-Acetylamino-4-tert.butyl-5-chloro-N-cyclohexyl-N-methyl-benzylamine by method A 26 gm of N-methyl-cyclohexylamine were added to 29 gm of 2-acetylamino-4-tert.butyl-5-chloro-benzyl bromide in 1.5 liters of carbon tetrachloride, and the mixture was refluxed for 2 hours. After cooling, the precipitated N-methyl-cyclohexylamine hydrobromide was filtered off, and the filtrate was evaporated. The residue was taken up in 2 N acetic acid, the solution was extracted with chloroform, and the acid phase was made alkaline with concentrated ammonia, extracted three times with chloroform, and the organic phase was evaporated. After column-chromatographic purification on silicagel with ethyl acetate/chloroform (1:1), the 2-acetylamino-4-tert.butyl-5-chloro-N-cyclohexyl-N-methyl-benzylamine thus obtained was recrystallized from absolute ethanol and recrystallized from ethanol, whereupon it had a melting point of 174–175.5° C.

EXAMPLE 6

2-Acetylamino-5-tert.butyl-N-cyclohexyl-N-methyl-benzyl-amine by method A 24 gm of N-methyl-cyclohexylamine were added to 23 gm of 2-acetylamino-5-tert.butyl-benzylbromide in 1.6 liters of carbon tetrachloride, and the mixture was refluxed for 1 hour. After cooling, the precipitated N-methyl-cyclohexyl-amine hydrobromide was filtered off, the filtrate was evaporated, and the crude product was purified chromatographically on silicagel with ethyl acetate. The corresponding fractions were combined and evaporated, and the 2-acetyl-amino-5-tert.butyl-N-cyclohexyl-N-methykl-benzylamine thus obtained was recrystallized from petroleumether, whereuponit had a melting point of 111–112.5° C.

EXAMPLE 7

4-Acetylamino-3-tert.butyl-N-cyclohexyl-N-methyl-benzyl-amine by method A 48 gm of N-methyl-cyclohexylamine were added to 56 gm of 4-acetylamino-3-tert.butyl-benzyl bromide in 500 ml of chloroform, and the mixture was refluxed for 1.5 hours. Subsequently, the reaction mixture was extracted three times with water, and the organic phase was evaporated. The residue was purified column-chromatograhically on silicagel with chloroform/methanol (5:1), and 4-acetylamino-3-tert.butyl-N-cyclohexyl-N-methyl-benzylamine hydrochloride, m.p. 240–243° C (decomp.), was crystallized from a solution of the purified base in absolute ethanol/ether by addition of absolute ethanolic hydrochloric acid.

EXAMPLE 8

5-Acetyl-2-acetylamino-N,N-dimethyl-benzylamine by method A 8.1 gm of dimethylamine were added to 21 gm of 5-acetyl-2-acetylamino-benzyl bromide in 500 ml of chloroform, and the mixture was stirred for 30 minutes. As soon as the exothermic reaction began, the undissolved substance dissolved. Subsequently, the reaction solution was extracted three times with water and twice with 2 N hydrochloric acid. The hydrochloric acid phase was extracted with chloroform, made alkaline with 2 N ammonia and again extracted twice with chloroform. The organic phase was evaporated, the residue was purified column-chromatographically on silicagel with ethyl acetate, and the corresponding fractions were combined and evaporated to dryness, whereby 5-acetyl-2-acetylamino-N,N-dimethyl benzylamine was obtained in crystalline form, having a melting point of 68–72° C.

EXAMPLE 9

2-Amino-3-bromo-N-cyclohexyl-5-fluoro-N-methyl-benzylamine and its hydrochloride by method A 3 gm of 2-amino-N-cyclohexyl-5-fluoro-N-methyl-benzylamine were dissolved in 30 ml of glacial acetic acid. While stirring the resulting solution, a solution of 1.98 gm (0.63 ml) of bromine in 20 ml of glacial acetic acid was added dropwise at room temperature. After the addition was finished, stirring was continued for 10 minutes, and then, while cooling on ice, 10 N sodium hydroxide was added until pH 9 was reached, whereupon the mixture was extracted twice with 150 ml of methylene chloride each. The united methylene chloride extracts were washed with water, dried over sodium sulfate and evaporated to dryness in vacuo. The residue were dissolved in absolute ethanol, and the resulting solution was acidified with ethanolic hydrochloric acid to pH 3. The precipitate formed thereby was vacuum-filtered off and recrystallized from a mixture of absolute ethanol and ether, yielding the hydrochloride of 2-amino-3-bromo-N-cyclohexyl-5-fluoro-N-methyl-benzylamine, m.p. 222–224° C.

EXAMPLE 10

2-Amino-3-bromo-5-tert.butyl-N-cyclohexyl-N-methyl-benzylamine and its hydrochloride by method B 10 gm of 2-amino-5-tert.butyl-N-cyclohexyl-N-methyl-benzylamine were dissolved in 50 ml of 90% acetic acid, and the solution as admixed with 5.8 gm of bromine dropwise at room temperature. Subsequently, the reaction solution was stirred for 30 minutes, then diluted with 200 ml of water, made alkaline with concentrated ammonia, and extracted three times with chloroform. The organic phase was evaporated, the residue was purified column-chromatographically on silicagel with chloroform/ethyl acetate (5:1), and 2-amino-3-bromo-5-tert.butyl-N-cyclohexyl-N-methyl-benzylamine hydrochloride, m.p. 214–215° C (decomp.), was crystallized from a solution of the purified residue in ethanol/ether by addition of ethanolic hydrochloric acid.

EXAMPLE 11

5-Acetyl-2-amino-3-bromo-N,N-dimethyl-benzylamine by method B 9.0 gm of bromine were added dropwise to a solution of 12.8 gm of 5-acetyl-2-amino-N,N-dimethyl-benzylamine hydrochloride in 100 ml of 80% acetic acid. Subsequently, the reaction mixture was made alkaline with 2 N ammonia, extracted twice with chloroform, and the organic extract was evaporated. By recrystallization of the residue from ethanol/water, 5-acetyl-2-amino-3-bromo-N,N-dimethyl-benzylamine, m.p. 92–95° C, was obtained.

EXAMPLE 12

2-Amino-5-chloro-N-cyclohexyl-N-methyl-3-trifluoromethyl-benzylamine and its hydrochloride by method B A solution of 9.5 gm of 2-amino-N-cyclohexyl-N-methyl-3-trifluoromethyl-benzylamine and 3 ml of pyridine in 40 ml of tetrahydrofuran was cooled to −10° C, and while stirring at this temperature it was admixed in the course of 20 minutes with a solution of 9.1 gm of iodobenzene dichloride in 80 ml of tetrahydrofuran. After stirring it for 4.5 hours at 0 to −10° C, the mixture was allowed to stand for 18 hours at 20° C. Thereafter, the reaction mixture was diluted with water and extracted with chloroform. The organic phase was washed with aqueous potassium carbonate and water, and after drying it over magnesium sulfate, the solution was evaporated in vacuo, and the oily residue, the free base 2-amino-5-chloro-N-cyclohexyl-N-methyl-3-trifluoromethyl-benzylamine, was taken up in ethyl acetate. The hydrochloride of the base was precipitated from this solution with isopropanolic hydrochloric acid. After recrystallizing the salt three times from ethanol in the presence of charcoal, colorless crystals were obtained which had a melting point of 260–262° C.

EXAMPLE 13

2-Amino-N,N-diethyl-3-methyl-benzylamine and its hydrochloride by method C 8 gm of 2-acetylamino-N,N-diethyl-3-methyl-benzylamine were dissolved in 300 ml of 2 N hydrochloric acid, and the solution was refluxed for 14 hours. Thereafter, the solution was decolorized with charcoal and was then made alkaline with concentrated ammonia. The resulting mixture was extracted three times with chloroform, the combined organic extracts were evaporated, and the residue was purified column-chromatographically on silicagel with ethyl acetate. The raw free base thus obtained was dissolved in acetone/ethanol, and the solution was neutralized with ethanolic hydrochloric acid, whereby 2-amino-N,N-diethyl-3-methyl-benzylamine hydrochloride, m.p. 182–184° C, crystallized out.

EXAMPLE 14

2-Amino-5-bromo-N,N-diethyl-3-diethylaminomethyl-benzylamine and its dihydrochloride by method C 11.5 gm of 2-acetylamino-5-bromo-N,N-diethyl-3-diethylaminomethyl-benzylamine were dissolved in 250 ml of 2N hydrochloric acid, and the solution was refluxed for 14 hours. Thereafter, the reaction solution was decolorized with charcoal, filtered, and the filtrate was made alkaline with concentrated ammonia, was then extracted three times with chloroform, and the combined organic extracts were evaporated. The residue was purified column-chromatographically on silicagel with chloroform/ethyl acetate (1:2). The united fractions containing the desired compound were evaporated, the residue was dissolved in absolute ethanol, and the solution was weakly acidified with absolute ethanolic hydrochloric acid, whereupon 2-amino-5-bromo-N,N-diethyl-3-diethylamino-methyl-benzylamine dihydrochloride, m.p. 213.5–215° C, crystallized out.

EXAMPLE 15

2-Amino-5-bromo-4-tert.butyl-N-cyclohexyl-N-methyl-benzylamine and its hydrochloride by method C 5 gm of 2-acetylamino-5-bromo-4-tert.butyl-N-cyclohexyl-N-methyl-benzylamine were refluxed in a mixture of 50 ml of ethanol and 50 ml of concentrated hydrochloric acid for 15 hours. Thereafter, the reaction mixture was made alkaline with concentrated ammonia and was then extracted three times with chloroform. The combined organic extracts were evaporated, the residue was purified column-chromatographically on silicagel with ethyl acetate, and 2-amino-5-bromo-4-tert.butyl-N-cyclohexyl-N-methyl-benzylamine hydrochloride, m.p. 202–202.5° C (decomp.), was crystallized from a solution of the purified residue in ethanol/ether by addition of ethanolic hydrochloric acid.

EXAMPLE 16

2-Amino-5-tert.butyl-N-cyclohexyl-N-methyl-benzylamine and its hydrochloride by method C 15 gm of 2-acetylamino-5-tert.butyl-N-cyclohexyl-N-methyl-benzylamine were refluxed in 0.5 liter of 4 N hydrochloric acid for 14 hours. Subsequently, the solution was made alkaline with concentrated ammonia, extracted three times with chloroform, and the combined organic extracts were evaporated. The residue was purified column-chromatographically on silicagel with ethyl acetate, and 2-amino-5-tert.butyl-N-cyclohexyl-N-methyl-benzylamine hydrochloride, m.p. 144–146° C, was crystallized from a solution of the purified residue in acetone/ether by addition of ethanolic hydrochloric acid.

EXAMPLE 17

4-Amino-3-tert.butyl-N-cyclohexyl-N-methyl-benzylamine and its dihydrochloride by method C 20 gm of 4-acetylamino-3-tert.butyl-N-cyclohexyl-N-methyl-benzylamine were refluxed in 200 ml of 3 N hydrochloric acid for 6 hours. Then, the reaction solution was made alkaline with concentrated ammonia, extracted three times with chloroform, and the combined organic extracts were evaporated. After addition of absolute ethanolic hydrochloric acid, 4-amino-3-tert-.butyl-N-cyclohexyl-N-methyl-benzylamine dihydrochloride, m.p. 197–199° C (decomp.) crystallized from a solution of the residue in absolute ethanol/ether.

EXAMPLE 18

5-Acetyl-2-amino-N,N-dimethyl-benzylamine and its hydrochloride by method C 22.5 gm of 5-acetyl-2-acetylamino-N,N-dimethyl-benzylamine were dissolved in a solution of 8 gm of sodium hydroxide in 400 ml of 50% ethanol, and the solution was heated at 70–80° C for 5 hours. Subsequently, the reaction solution was diluted with water, extracted three times with chloroform, and the combined organic extracts were evaporated. The residue was dissolved in absolute ethanol, and the solution was neutralized with absolute ethanolic hydrochloric acid, whereupon 5-acetyl-2-amino-N,N-dimethyl-benzylamine hydrochloride, m.p. 209–215° C (decomp.), crystallized out.

EXAMPLE 19

N-[2-Amino-3-bromo-5-(1'-hydroxy-ethyl)-benzyl]-hexamethyl-amine by method D 9 gm of N-(5-acetyl-2-amino-3-bromo-benzyl)-hexamethyleneamine were dissolved in a mixture of 250 ml of ethanol and 100 ml of water, the solution was admixed, while stirring, with 6 gm of sodium borohydride in portions, and the mixture was allowed to stand for 15 hours. Subsequently, the reaction solution was diluted with 300 ml of water, extracted three times with chloroform, and the combined organic extracts were extracted with water and evaporated. The residue was purified column-chromatographically on silicagel with ethylacetate, whereby N-[2-amino-3-bromo-5-(1'-hydroxy-ethyl)-benzyl]-hexamethyleneamine was obtained in crystalline form. Upon recrystalization from isopropanol it had a melting point of 110–112° C.

EXAMPLE 20

N-Ethyl-2-amino-3-bromo-5-carboxy-N-cyclohexyl-benzylamine hydrochloride by method E 13 gm of N-ethyl-2-amino-3-bromo-5-carbethoxy-N-cyclohexyl-benzylamine were boiled with 100 ml of 6 N hydrochloric acid for 1 hour. Subsequently, the supernatant liquid was decanted from the oily phase which had formed at the bottom, and the solution was evaporated to dryness. The residue was recrystallized from methanol, yielding N-ethyl-2-amino-3-bromo-5-carboxy-N-cyclohexyl-benzylamine hydrochloride, m.p. 227–229° C.

EXAMPLE 21

2-Amino-3-bromo-5-carbamoyl-N,N-diethyl-benzylamine by method E 11 gm of 2-amino-3-bromo-5-cyano-N,N-diethyl-benzylamine were refluxed with a mixture of 70 ml of ethanol and 100 ml of 5 N sodium hydroxide. After cooling, the reaction solution was diluted with 100 ml of water and extracted with chloroform. The chloroform extract was dried over sodium sulfate and evaporated, and the residue was recrystallized from isopropanol, yielding 2-amino-3-bromo-5-carbamoyl-N,N-diethyl-benzylamine, m.p. 140–142° C.

EXAMPLE 22

2-Acetamino-3-bromo-5-carbethoxy-N,N-diethyl-benzylamine and its hydrochloride 1 gm of 2-amino-3-bromo-5-carbethoxy-N,N-diethyl-benzylamine were dissolved in 2 ml of acetylchloride, and the solution was heated at 50° C for 1 hour. The excess acetylchloride was evaporated in vacuo, the residue was distributed between cold dilute ammonia and chloroform, the chloroform solution was evaporated, the residue was purified by chromatography on silicagel (elution agent: ethyl acetate), the evaporation residue of the eluate was dissolved in isopropanol, and 2-acetamino-3-bromo-5-carbethoxy-N,N-diethyl-benzylamine hydrochloride, m.p. 190–194° C, was caused to crystallize out by addition of isopropanolic hydrochloric acid and ether.

EXAMPLE 23

2-Acetamino-3-bromo-N,N-diethyl-5-methyl-benzylamine hydrochloride 1.53 gm of 2-amino-3-bromo-N,N-diethyl-5-methyl-benzylamine hydrochloride were dissolved in 50 ml of acetic acid anhydride at 75° C. The solution was evaporated to dryness in vacuo, and the residue was recrystallized from ethanol, yielding 2-acetamino-3-bromo-N,N-diethyl-5-methyl-benzylamine hydrochloride, m.p. 170–172° C.

EXAMPLE 24

2-Acetamino-3-bromo-N,5-dimethyl-N-(trans-4'-hydroxy-cyclohexyl)-benzylamine and its hydrochloride 2.2 gm of 2-amino-3-bromo-N,5-dimethyl-N-(trans-4'-hydroxy-cyclohexyl)-benzylamine were dissolved in 100 ml of methanol, and the solution was heated to the boiling point. In the course of 2 hours 75 ml of acetic anhydride were added, and the resulting methyl acetate was distilled off. The residual solution was evaporated to dryness in vacuo, and after addition of some more methanol it was evaporated again. The residue was dissolved in ethanol and converted with ethanolic hydrochloric acid into 2-acetamino-3-bromo-N,5-dimethyl-N-(trans-4'-hydroxy-cyclohexyl)-benzylamine hydrochloride, m.p. 246–248° C.

EXAMPLE 25

2-Acetamino-5-carbethoxy-N,N-diethyl-benzylamine by method A 30 gm of 2-acetamino-5-carbethoxy-benzyl bromide were dissolved in a mixture of 400 ml of chloroform and 100 ml of ethanol, and the solution was refluxed with 22 gm of diethylamine for 1 hour. Thereafter, the reaction solution was cooled, then evaporated in vacuo, the residue was distributed between a mixture of dilute ammonia and chloroform, and the chloroform phase was dried over sodium sulfate and evaporated in vacuo. The residue was purified by chromatography on silicagel (elution agent: ethyl acetate) and recrystallized from ethanol, yielding 2-acetamino-5-carbethoxy-N,N-diethyl-benzylamine, m.p. 57–59° C.

EXAMPLE 26

2-Amino-N-cyclohexyl-N-methyl-3-trifluoromethyl-benzylamine and its hydrochloride by method A 20 gm of 2-amino-3-trifluoromethyl-benzylalcohol were dissolved in 200 ml of chloroform, and while stirring it, the solution was admixed dropwise with 15.9 ml of thionylchloride in the course of 10 minutes. The resulting mixture was refluxed for 90 minutes, then cooled, and all volatile matter was carefully removed in vacuo. The residue was dissolved in 200 ml of chloroform, and while stirring the solution mechanically on an ice bath, 38.1 gm of N-methyl-cyclohexylamine were added within 10 minutes, and the resulting mixture was allowed to stand for 18 hours at 20° C. The reaction mixture was then washed with saturated aqueous potassium carbonate, dried, and the solvent was removed in vacuo. The oily evaporation residue was purified by chromatography on a silicagel column (flow agent: chloroform/methanol = 9:1), and the eluate was evaporated. The evaporation residue, which was oily again, was dissolved in a mixture of ether and ethyl acetate (1:1). Upon addition of isopropanolic hydrochloric acid to the solution, crystalline 2-amino-N-cyclohexyl-N-methyl-3-trifluoromethyl-benzylamine hydrochloride separated out, which was recrystallized twice from isopropanol, and then had a melting point of 203–206° C.

EXAMPLE 27

2-Amino-3-bromo-5-carbethoxy-N,N-diethyl-benzylamine and its hydrochloride by method B 80 gm of 2-amino-5-carbethoxy-N,N-diethyl-benzylamine were dissolved in a mixture of 300 ml of glacial acetic acid and 30 ml of water, and the solution was admixed dropwise, while stirring, with a solution of 40 gm of bromine in 40 ml of glacial acetic acid at room temperature, and the mixture was allowed to stand for 1 hour. Thereafter, it was poured over ice, make alkaline with ammonia and extracted with chloroform. The combined chloroform extracts were evaporated to dryness in vacuo, and the residue was purified by chromatography on silicagel (elution agent: ethyl acetate) and converted with isopropanolic hydrochloric acid into 2-amino-3-bromo-5-carbethoxy-N,N-diethyl-benzylamine hydrochloride, which was recrystallized from ethanol, whereupon it had a melting point of 165–168° C.

EXAMPLE 28

2-Amino-3-bromo-5-cyano-N-cyclohexyl-N-methyl-benzylamine and its hydrochloride by method B 7 gm of 2-amino-5-cyano-N-cyclohexyl-N-methyl-benzylamine were dissolved in 100 ml of 90% acetic acid, and while stirring the solution, it was admixed dropwise with a solution of 4 gm of bromine in 4 ml of glacial acetic acid. The resulting mixture was stirred for 1 hour at room temperature and for 30 minutes more at 60° C, then cooled, poured over ice, made alkaline with ammonia and extracted three times with chloroform. The combined chloroform extracts were evaporated in vacuo, the residue was dissolved in ethanol, and by addition of ethanolic hydrochloric acid 2-amino-3-bromo-5-cyano-N-cyclohexyl-N-methyl-benzylamine hydrochloride, m.p. 236–240° C, was caused to crystallize out.

EXAMPLE 29

2-Amino-5-chloro-N-cyclohexyl-3-methoxy-N-methyl-benzylamine and its hydrochloride by method B 11 gm of 2-amino-N-cyclohexyl-3-methoxy-N-methyl-benzylamine were dissolved in 100 ml of glacial acetic acid, and while stirring the solution, it was quickly admixed with a solution of 2.8 gm of chlorine in 50 ml of glacial acetic acid at room temperature. The resulting mixture was immediately poured into a sodium bisulfite solution, mixed with ice and made alkaline with 10 N sodium hydroxide. The precipitate formed thereby was extracted with chloroform, and the chloroform extract was washed with water, dried over sodium sulfate and evaporated to dryness in vacuo. The residue was chromatographed on silicagel with chloroform-/ethyl acetate (3:1). The obtained crude base was dissolved in absolute ethanol, and the solution was acidified with ethereal hydrochloric acid to pH 5–6 and admixed with petroleum ether. The precipitated hydrochloride was vacuum-filtered off and washed with a small quantity of petroleum ether, whereupon it had a melting point of 189–193° C (decomp.).

EXAMPLE 30

2-Amino-5-bromo-N-cyclohexyl-N-methyl-3-trifluoromethyl-benzylamine and its hydrochloride by method B 9.5 gm of 2-amino-N-cyclohexyl-N-methyl-3-trifluoromethyl-benzylamine were dissolved in 140 ml of 70% acetic acid, and the solution was admixed over a period of 5 minutes with 5.5 gm of bromine in 30 ml of glacial acetic acid, while stirring. After 90 minutes, the excess bromine was destroyed by addition of sodium bisulfite solution, and the mixture was then evaporated in vacuo. The residue was distributed between a mixture of ethyl acetate and saturated aqueous potassium carbonate, and the organic phase was dried and evaporated in vacuo again. The residual oil was dissolved in a mixture of ether and ethylacetate (1:1), and the hydrochloride of the above-named compound was precipitated by addition of isopropanolic hydrochloric acid. After recrystallizing it twice from ethanol, the hydrochloride had a melting point of 259–261° C.

EXAMPLE 31

2-Amino-5-carbethoxy-N,N-diethyl-benzylamine and its hydrochloride by method C 19 gm of 2-acetamino-5-carbethoxy-N,N-diethyl-benzylamine were dissolved in 100 ml of ethanol, and after addition of 60 ml of concentrated hydrochloric acid the mixture was refluxed for 1 hour. Thereafter the mixture was poured over ice, made alkaline with ammonia and extracted three times with chloroform. The combined chloroform extracts were dried over sodium sulfate and evaporated in vacuo, and the residue was purified by chromatography on silicagel (elution agent: ethyl acetate); by addition of isopropanolic hydrochloric acid, 2-amino-5-carbethoxy-N,N-diethyl-benzylamine hydrochloride was obtained, which was recrystallized from ethanol and then had a melting point of 138–142° C.

EXAMPLE 32

2-Amino-5-carboxy-N-cyclohexyl-N-methyl-benzylamine by method E

A mixture of 21 gm of 2-acetamino-5-carbethoxy-N-cyclohexyl-N-methyl-benzylamine, 100 ml of ethanol, 90 ml of water and 60 ml of concentrated hydrochloric acid was refluxed for 1 hour. Thereafter, the reaction solution was cooled, poured over ice, made alkaline with ammonia and extracted three times with chloroform. The aqueous alkaline phase was evaporated to dryness in vacuo, the residue was thoroughly stirred with ethanol, and the mixture was filtered. The filtrate was evaporated to dryness in vacuo, and the residue was recrystallized from ethanol, yielding 2-amino-5-carboxy-N-cyclohexyl-N-methyl-benzylamine, m.p. 200–205° C.

EXAMPLE 33

2-Amino-5-carbamoyl-N,N-diethyl-benzylamine by method E

A mixture of 10 gm of 2-acetamino-5-cyano-N,N-diethyl-benzylamine, 100 ml of 5 N sodium hydroxide and 70 ml of ethanol was boiled for 4 hours. Thereafter, the reaction solution was cooled, diluted with 200 ml of water and extracted three times with 250 ml of chloroform each. The combined chloroform extracts were dried over sodium sulfate and evaporated in vacuo, and the residue was recrystallized from ethanol. The 2-amino-5-carbamoyl-N,N-diethyl-benzylamine of m.p. 129–131° C was obtained.

EXAMPLE 34

2-Amino-N-ethyl-N-cyclohexyl-5-methyl-benzylamine and its hydrochloride by method C A mixture of 2 gm of 2-acetamino-N-cyclohexyl-5-methyl-benzylamine and 50 ml of concentrated hydrochloric acid was heated at 90° C for 1.5 hours. Thereafter, the reaction solution was cooled, poured over ice, made alkaline with sodium hydroxide, extracted with chloroform, and the chloroform extract was evaporated in vacuo. The residue was dissolved in ethanol, and upon addition of ethanolic hydrochloric acid, 2-amino-N-ethyl-N-cyclohexyl-5-methyl-benzylamine hydrochloride, m.p. 189–181° C (decomp.), was obtained.

EXAMPLE 35

2-Amino-3-chloro-N-cyclohexyl-5-fluoro-N-methyl-benzylamine and its hydrochloride by method E A solution of 9.1 gm of 2-amino-3-chloro-N-cyclohexyl-5-fluoro-N-methyl-benzamide in 300 ml of absolute ether was added dropwise to a suspension of 3.8 gm of lithium aluminum hydride in 200 ml of absolute ether, while stirring. The resulting mixture was refluxed for 1 hour and then cooled on an ice bath. The excess lithium aluminum hydride was carefully decomposed with water in an atmosphere of nitrogen. The organic phase as decanted from the precipitate, dried over sodium sulfate, and acidified with ethereal hydrochloric acid, whereby 2-amino-3-chloro-N-cyclohexyl-5-fluoro-N-methyl-benzylamine hydrochloride precipitated out, which was recrystallized from absolute ethanol/ether, whereupon it had a melting point of 190–192° C.

EXAMPLE 36

2-Amino-N-tert.butyl-5-carbethoxy-benzylamine by method E 3.4 gm of 2-amino-N-benzyl-N-tert.butyl-5-carbethoxy-benzylamine were dissolved in 50 ml of ethanol. Ethanolic hydrochloric acid was added to the solution until a pH of about 2 was reached. The solution was then hydrogenated in the presence of palladized (10%) charcoal. After absorption of 1 mol of hydrogen, the hydrogenation was terminated, the catalyst was filtered off, the filtrate was evaporated to dryness in vacuo, and the residue was distributed between a mixture of dilute ammonia and chloroform. The chloroform phase was dried and evaporated to dryness, and the residue was recrystallized from ethanol, yielding 2-amino-N-tert.butyl-5-carbethoxy-benzylamine, m.p. 77–79° C.

EXAMPLE 37

2-Acetamino-N-tert.butyl-5-carbethoxy-benzylamine, m.p. 136–139° C, was prepared from 2-acetamino-5-carbethoxy-benzyl bromide and tert.butylamine analogous to Example 25.

EXAMPLE 38

2-Amino-N-tert.butyl-5-carbethoxy-benzylamine, m.p. 77–79° C, was prepared by hydrolysis of 2-acetamino-N-tert.butyl-5-carbethoxy-benzylamine in ethanolic hydrochloric acid analogous to Example 31.

EXAMPLE 39

2-Amino-3-bromo-N-tert.butyl-5-carbethoxy-benzylamine, m.p. 78–81° C, was prepared from 1-amino-N-tert.butyl-5-carbethoxy-benzylamine and bromine analogous to Example 27.

EXAMPLE 40

2-Acetamino-5-carbethoxy-N-cyclohexyl-N-methyl-benzylamine, m.p. 71–74° C, was prepared from 2-acetamino-5-carbethoxy-benzyl bromide and N-methyl-cyclohexylamine analogous to Example 25

EXAMPLE 41

2-Amino-5-carbethoxy-N-cyclohexyl-N-methyl-benzylamine and its hydrochloride, m.p. 160–170° C, was prepared by hydrolysis of 2-acetamino-5-carbethoxy-N-cyclohexyl-N-methyl-benzylamine in ethanolic hydrochloric acid analogous to Example 31.

EXAMPLE 42

2-Amino-3-bromo-5-carbethoxy-N-cyclohexyl-N-methyl-benzylamine and its hydrochloride, m.p. 212–215° C, were prepared from 2-amino-5-carbethoxy-N-cyclohexyl-N-methyl-benzylamine and bromine analogous to Example 27.

EXAMPLE 43

2-Amino-5-carbethoxy-3-chloro-N-cyclohexyl-N-methyl-benzylamine and its hydrochloride, m.p. 207–209° C, were prepared from 2-amino-5-carbethoxy-N-cyclohexyl-N-methyl-benzylamine and chlorine analogous to Example 27.

EXAMPLE 44

2-Acetamino-3-bromo-5-carbethoxy-N-cyclohexyl-N-methyl-benzylamine and its hydrochloride, m.p. 220–223° C, was prepared from 2-amino-3-bromo-5-carbethoxy-N-cyclohexyl-N-methyl-benzylamine and acetylchloride analogous to Example 22.

EXAMPLE 45

2-Acetamino-N-ethyl-5-carbethoxy-N-cyclohexyl-benzylamine, m.p. 92–95° C, was prepared from 2-acetamino-5-carbethoxy-benzyl bromide and N-ethyl-cyclohexylamine analogous to Example 25.

EXAMPLE 46

N-Ethyl-2-amino-5-carbethoxy-N-cyclohexyl-benzylamine and its dihydrochloride, m.p. 188–194° C, were prepared by hydrolysis from 2-acetamino-N-ethyl-5-carbethoxy-N-cyclohexyl-benzylamine in ethanolic hydrochloric acid analogous to Example 31.

EXAMPLE 47

N-Ethyl-2-amino-3-bromo-5-carbethoxy-N-cyclohexyl-benzylamine, m.p. 66–68° C, was prepared from N-ethyl-2-amino-5-carbethoxy-N-cyclohexyl-benzylamine and bromine analogous to Example 27.

EXAMPLE 48

N-Ethyl-2-amino-5-carbethoxy-3-chloro-N-cyclohexyl-benzylamine and its hydrochloride, m.p. 165–170° C, were prepared from N-ethyl-2-amino-5-carbethoxy-N-cyclohexyl-benzylamine and chlorine analogous to Example 27.

EXAMPLE 49

N-(2-Acetamino-5-carbethoxy-benzyl)-hexamethyleneamine, m.p. 100–102° C, was prepared from 2-acetamino-5-carbethoxy-benzyl bromide and hexamethyleneamine analogous to Example 25.

EXAMPLE 50

2-Amino-N-tert.butyl-5-carbamoyl-benzylamine and its hydrochloride, m.p. 120–130° C, were prepared by hydrolysis of 2-acetamino-N-tert.butyl-5-cyano-benzylamine in aqueous sodium hydroxide analogous to Example 33.

EXAMPLE 51

2-Amino-3-bromo-N-tert.butyl-5-carbamoyl-benzylamine and its hydrochloride, m.p. 160–170° C, were prepared by hydrolysis of 2-amino-3-bromo-N-tert.butyl-5-cyano-benzylamine in aqueous sodium hydroxide analogous to Example 21.

EXAMPLE 52

2-Amino-5-carbamoyl-N-cyclohexyl-N-methyl-benzylamine, m.p. 142–143° C, was prepared by hydrolysis of 2-amino-5-cyano-N-cyclohexyl-N-methyl-benzylamine in aqueous sodium hydroxide analogous to Example 21.

EXAMPLE 53

2-Amino-3-bromo-5-carbamoyl-N-cyclohexyl-N-methyl-benzylamine, m.p. 150–152° C, was prepared by hydrolysis of 2-amino-3-bromo-5-cyano-N-cyclohexyl-N-methyl-benzylamine in aqueous sodium hydroxide analogous to Example 21.

EXAMPLE 54

2-Acetamino-3-bromo-5-carbamoyl-N-cyclohexyl-N-methyl-benzylamine, m.p. 185–190° C, was prepared from 2-amino-3-bromo-5-carbamoyl-N-cyclohexyl-N-methyl-benzylamine and acetylchloride analogous to Example 22.

EXAMPLE 55

N-Ethyl-2-amino-5-carbamoyl-N-cyclohexyl-benzylamine, m.p. 136–138° C, was prepared by hydrolysis of N-ethyl-2-acetamino-5-cyano-N-cyclohexyl-benzylamine in aqueous sodium hydroxide analogous to Example 33.

EXAMPLE 56

N-Ethyl-2-amino-3-bromo-5-carbamoyl-N-cyclohexyl-benzylamine, m.p. 144–146° C, was prepared by hydrolysis of N-ethyl-2-amino-3-bromo-5-cyano-N-cyclohexyl-benzylamine in aqueous sodium hydroxide analogous to Example 21.

EXAMPLE 57

N-(2-Amino-5-carbamoyl-benzyl)-hexamethyleneamine, m.p. 115–118° C, was prepared by hydrolysis of N-(2-amino-5-cyano-benzyl)-hexamethyleneamine in aqueous sodium hydroxide analogous to Example 21.

EXAMPLE 58

N-(2-Amino-3-bromo-5-carbamoyl-benzyl)-hexamethyleneamine, m.p. 155–157° C, was prepared by hydrolysis of N-(2-amino-3-bromo-5-cyano-benzyl)-hexamethyleneamine in aqueous sodium hydroxide analogous to Example 21.

EXAMPLE 59

2-Amino-5-carboxy-N,N-diethyl-benzylamine and its hydrochloride, m.p. 194–198° C, were prepared by hydrolysis of 2-amino-5-carbethoxy-N,N-diethyl-benzylamine in hydrochloric acid analogous to Example 20.

EXAMPLE 60

2-Amino-3-bromo-5-carboxy-N,N-diethyl-benzylamine and its hydrochloride, m.p. 233–234° C (decomp.), were prepared by hydrolysis of 2-amino-3-bromo-5-carbethoxy-N,N-diethyl-benzylamine in hydrochloric acid analogous to Example 20.

EXAMPLE 61

2-Amino-N-tert.butyl-5-carboxy-benzylamine and its hydrochloride, m.p. 220–230° C, were prepared by hydrolysis of 2-acetamino-N-tert.butyl-5-carbethoxy-benzylamine in hydrochloric acid analogous to Example 32.

EXAMPLE 62

2-Amino-3-bromo-N-tert.butyl-5-carboxy-benzylamine and its hydrochloride, m.p. 270–280° C (decomp.), were prepared by hydrolysis of 2-amino-3-bromo-N-tert.butyl-5-carbethoxy-benzylamine in hydrochloric acid analogous to Example 20.

EXAMPLE 63

2-Acetamino-5-carboxy-N-cyclohexyl-N-methyl-benzylamine and its hydrochloride, m.p. 228–232° C, were prepared from 2-amino-5-carboxy-N-cyclohexyl-N-methyl-benzylamine and acetylchloride analogous to Example 22.

EXAMPLE 64

2-Amino-3-bromo-5-carboxy-N-cyclohexyl-N-methyl-benzylamine and its hydrochloride, m.p. 230–240° C, were prepared by hydrolysis of 2-amino-3-bromo-5-carbethoxy-N-cyclohexyl-N-methyl-benzylamine in hydrochloric acid analogous to Example 20.

EXAMPLE 65

N-Ethyl-2-amino-5-carboxy-N-cyclohexyl-benzylamine and its dihydrochloride, m.p. 175–181° C, were prepared by hydrolysis of N-ethyl-2-amino-5-carbethoxy-N-cyclohexyl-benzylamine in hydrochloric acid analogous to Example 20.

EXAMPLE 66

N-Ethyl-2-amino-5-carboxy-3-chloro-N-cyclohexyl-benzylamine and its hydrochloride, m.p. 228–232° C, were prepared by hydrolysis of N-ethyl-2-amino-5-carbethoxy-3-chloro-N-cyclohexyl-benzylamine in hydrochloric acid analogous to Example 20.

EXAMPLE 67

2-Acetamino-5-cyano-N,N-dimethyl-benzylamine and its hydrochloride, m.p. 244–245° C (decomp.), were prepared from 2-acetamino-5-cyano-benzylbromide and dimethylamine analogous to Example 25.

EXAMPLE 68

2-Amino-5-cyano-N,N-dimethyl-benzylamine and its hydrochloride, m.p. 240–241° C, were prepared by hydrolysis of 2-acetamino-5-cyano-N,N-dimethyl-benzylamine in hydrochloric acid analogous to Example 34.

EXAMPLE 69

2-Amino-3-bromo-5-cyano-N,N-dimethyl-benzylamine and its hydrochloride, m.p. 250–255° C (decomp.), were prepared from 2-amino-5-cyano-N,N-dimethyl-benzylamine and bromine analogous to Example 28.

EXAMPLE 70

2-Acetamino-5-cyano-N,N-diethyl-benzylamine, m.p. 80–82° C, was prepared from 2-acetamino-5-cyano-benzylbromide and diethylamine analogous to Example 25.

EXAMPLE 71

2-Amino-5-cyano-N,N-diethyl-benzylamine and its hydrochloride, m.p. 241–244° C, were prepared by hydrolysis of 2-acetamino-5-cyano-N,N-diethyl-benzylamine in hydrochloric acid analogous to Example 34.

EXAMPLE 72

2-Amino-3-bromo-5-cyano-N,N-diethyl-benzylamine and its hydrochloride, m.p. 226–229° C, were prepared from 2-amino-5-cyano-N,N-diethyl-benzylamine and bromine analogous to Example 28.

EXAMPLE 73

2-Acetamino-5-cyano-N,N-di-n-propyl-benzylamine, m.p. 80–82° C, was prepared from 2-acetamino-5-cyano-benzylbromide and di-n-propylamine analogous to Example 25.

EXAMPLE 74

2-Amino-5-cyano-N,N-dipropyl-benzylamine and its hydrochloride, m.p. 215–219° C, were prepared by hydrolysis of 2-acetamino-5-cyano-N,N-dipropyl-benzylamine in hydrochloric acid analogous to Example 34.

EXAMPLE 75

2-Acetamino-N-tert.butyl-5-cyano-benzylamine and its hydrochloride, m.p. 260–265° C, were prepared from 2-acetamino-5-cyano-benzylbromide and tert.butylamine analogous to Example 25.

EXAMPLE 76

2-Amino-N-tert.butyl-5-cyano-benzylamine and its hydrochloride, m.p. 233–238° C, were prepared by hydrolysis of 2-acetamino-N-tert.butyl-5-cyano-benzylamine in hydrochloric acid analogous to Example 34.

EXAMPLE 77

2-Amino-3-bromo-N-tert.butyl-5-cyano-benzylamine, m.p. 78–80° C, was prepared from 2-amino-N-tert.butyl-5-cyano-benzylamine and bromine analogous to Example 28.

EXAMPLE 78

2-Acetamino-5-cyano-N-cyclohexyl-N-methyl-benzylamine, m.p. 116–118° C, was prepared from 2-acetamino-5-cyano-benzyl bromide and N-methyl-cyclohexylamine analogous to Example 25.

EXAMPLE 79

2-Amino-5-cyano-N-cyclohexyl-N-methyl-benzylamine and its hydrochloride, m.p. 207–211° C, were prepared by hydrolysis of 2-acetamino-5-cyano-N-cyclohexyl-N-methyl-benzylamine in hydrochloric acid analogous to Example 34.

EXAMPLE 80

2-Acetamino-3-bromo-5-cyano-N-cyclohexyl-N-methyl-benzylamine, m.p. 101–103° C, was prepared from 2-amino-3-bromo-5-cyano-N-cyclohexyl-N-methyl-benzylamine and acetylchloride analogous to Example 22.

EXAMPLE 81

2-Acetamino-N-ethyl-5-cyano-N-cyclohexyl-benzylamine, m.p. 85–88° C, was prepared from 2-acetamino-5-cyano-benzyl bromide and N-ethyl-cyclohexylamine analogous to Example 25.

EXAMPLE 82

2-Amino-N-ethyl-5-cyano-N-cyclohexyl-benzylamine and its dihydrochloride, m.p. 201–206° C, were prepared by hydrolysis of 2-acetamino-N-ethyl-5-cyano-N-cyclohexyl-benzylamine in hydrochloric acid analogous to Example 34.

EXAMPLE 83

2-Amino-3-bromo-5-cyano-N-cyclohexyl-N-ethyl-benzylamine and its hydrochloride, m.p. 194–197° C, were prepared from 2-amino-5-cyano-N-cyclohexyl-N-ethyl-benzylamine and bromine analogous to Example 28.

EXAMPLE 84

2-Acetamino-N-benzyl-5-cyano-N-ethyl-benzylamine, m.p. 112–113° C, was prepared from 2-acetamino-5-cyano-benzyl bromide and N-ethyl-benzylamine analogous to Example 25.

EXAMPLE 85

2-Amino-N-ethyl-N-benzyl-5-cyano-benzylamine, m.p. 107–108° C, was prepared by hydrolysis of 2-acetamino-N-ethyl-N-benzyl-5-cyano-benzylamine in hydrochloric acid analogous to Example 34.

EXAMPLE 86

2-Amino-N-benzyl-3-bromo-5-cyano-N-ethyl-benzylamine, m.p. 89–90° C, was prepared from 2-amino-N-benzyl-5-cyano-N-ethyl-benzylamine and bromine analogous to Example 28.

EXAMPLE 87

2-Acetamino-N-benzyl-5-cyano-N-n-propyl-benzylamine, m.p. 109–111° C, was prepared from 2-acetamino-5-cyano-benzyl bromide and N-n-propyl-benzylamine analogous to Example 25.

EXAMPLE 88

2-Amino-N-benzyl-5-cyano-N-n-propyl-benzylamine, m.p. 63–64° C, was prepared by hydrolysis of 2-acetamino-N-benzyl-5-cyano-N-n-propyl-benzylamine in hydrochloric acid analogous to Example 34.

EXAMPLE 89

2-Amino-N-benzyl-3-bromo-5-cyano-N-n-propyl-benzylamine, m.p. 96–98° C, was prepared from 2-amino-N-benzyl-5-cyano-N-n-propyl-benzylamine and bromine analogous to Example 28.

EXAMPLE 90

2-Acetamino-N-benzyl-N-n-butyl-5-cyano-benzylamine, m.p. 65–66° C, was prepared from 2-acetamino-5-cyano-benzyl bromide and N-n-butyl-benzylamine analogous to Example 25.

EXAMPLE 91

2-Amino-N-benzyl-3-bromo-N-n-butyl-5-cyano-benzylamine, m.p. 71–73° C, was prepared from 2-amino-N-benzyl-N-n-butyl-5-cyano-benzylamine and bromine analogous to Example 28.

EXAMPLE 92

N-(2-Acetamino-5-cyano-benzyl)-hexamethyleneamine; m.p. 108–110° C, was prepared from 2-acetamino-5-cyano-benzyl bromide and hexamethyleneamine analogous to Example 25.

EXAMPLE 93

N-(2-Amino-5-cyano-benzyl)-hexamethyleneamine and its hydrochloride, m.p. 228–232° C, were prepared by hydrolysis of N-(2-acetamino-5-cyano-benzyl)-hexamethyleneamine in hydrochloric acid analogous to Example 34.

EXAMPLE 94

N-(2-Amino-3-bromo-5-cyano-benzyl)-hexamethyleneamine and its hydrochloride, m.p. 172–176° C, were prepared from N-(2-amino-5-cyano-benzyl)-hexamethyleneamine and bromine analogous to Example 28.

EXAMPLE 95

2-Acetamino-3-bromo-N,N,5-trimethyl-benzylamine, m.p. 89–91° C, was prepared from 2-amino-3-bromo-N,N,5-trimethyl-benzylamine and acetic acid anhydride analogous to Example 23.

EXAMPLE 96

2-Amino-3-bromo-N,N,5-trimethyl-benzylamine and its hydrochloride, m.p. 216–217° C, were prepared from 2-amino-3-bromo-5-methyl-benzyl alcohol, thionyl chloride and dimethylamine analogous to Example 1.

EXAMPLE 97

2-Acetamino-3-bromo-N,5-dimethyl-N-ethyl-benzylamine, m.p. 81–83° C, was prepared from 2-amino-3-bromo-N,5-dimethyl-N-ethyl-benzylamine and acetic acid anhydride analogous to Example 23.

EXAMPLE 98

2-Amino-3-bromo-N,5-dimethyl-N-ethyl-benzylamine and its hydrochloride, m.p. 199–200° C, were prepared from 2-amino-3-bromo-5-methyl-benzyl alcohol, thionyl chloride and N-methyl-ethylamine analogous to Example 1.

EXAMPLE 99

2-Acetamino-N,N-diethyl-5-methyl-benzylamine and its hydrochloride, m.p. 184–186° C, were prepared from 2-acetamino-5-methyl-benzyl bromide and diethylamine analogous to Example 6.

EXAMPLE 100

2-Amino-N,N-diethyl-5-methyl-benzylamine and its dihydrochloride, m.p. 193–195° C, were prepared by hydrolysis of 2-acetamino-N,N-diethyl-5-methyl-benzylamine in hydrochloric acid analogous to Example 34.

EXAMPLE 101

2-Amino-3-bromo-N,N-diethyl-5-methyl-benzylamine and its hydrochloride, m.p. 205–207° C, were prepared from 2-amino-3-bromo-5-methyl-benzyl alcohol, thionyl chloride and diethylamine analogous to Example 1.

EXAMPLE 102

2-Acetamino-N-cyclohexyl-N,5-dimethyl-benzylamine and its hydrochloride, m.p. 222–223° C, were prepared from 2-acetamino-5-methyl-benzyl bromide and N-methyl-cyclohexylamine analogous to Example 6.

EXAMPLE 103

2-Amino-N-cyclohexyl-N,5-dimethyl-benzylamine and its dihydrochloride, m.p. 203–205° C, were prepared by hydrolysis of 2-acetamino-N-cyclohexyl-N,5-dimethyl-benzylamine in hydrochloric acid analogous to Example 34.

EXAMPLE 104

2-Amino-3-bromo-N-cyclohexyl-N,5-dimethyl-benzylamine and its hydrochloride, m.p. 223–224° C, were prepared from 2-amino-3-bromo-5-methyl-benzyl alcohol, thionyl chloride and N-methyl-cyclohexylamine analogous to Example 1.

EXAMPLE 105

2-Acetamino-3-bromo-N,5-dimethyl-N-(cis-3'-hydroxy-cyclohexyl)-benzylamine and its hydrochloride, m.p. 96–97° C, were prepared from 2-amino-3-bromo-N,5-dimethyl-N-(cis-3'-hydroxy-cyclohexyl)-benzylamine and acetic acid anhydride analogous to Example 24.

EXAMPLE 106

2-Amino-3-bromo-N,5-dimethyl-N-(cis-3'-hydroxy-cyclohexyl)-benzylamine and its hydrochloride, m.p. 198° C, were prepared from 2-amino-3-bromo-5-methyl-benzyl alcohol, thionyl chloride and N-methyl-cis-3-hydroxy-cyclohexylamine analogous to Example 1.

EXAMPLE 107

2-Acetamino-N-cyclohexyl-N-ethyl-5-methyl-benzylamine and its hydrochloride, m.p. 224–225° C, were prepared from 2-acetamino-5-methyl-benzyl bromide and N-ethyl-cyclohexylamine analogous to Example 6.

EXAMPLE 108

2-Amino-3-bromo-N-cyclohexyl-N-ethyl-5-methyl-benzylamine and its hydrochloride, m.p. 186° C, were prepared from 2-amino-3-bromo-5-methyl-benzyl alcohol, thionyl chloride and N-ethyl-cyclohexylamine analogous to Example 1.

EXAMPLE 109

2-Amino-3-bromo-N,5-dimethyl-N-(trans-4'-hydroxy-cyclohexyl)-benzylamine and its hydrochloride, m.p. 212° C, were prepared from 2-amino-3-bromo-5-methyl-benzyl alcohol, thionyl chloride and N-methyl-trans-4-hydroxy-cyclohexylamine analogous to Example 1.

EXAMPLE 110

2-Acetamino-N-benzyl-3-bromo-N,5-dimethyl-benzylamine and its hydrochloride, m.p. 210–212° C, were prepared from 2-amino-N-benzyl-3-bromo-N,5-dimethyl-benzylamine and acetic acid anhydride analogous to Example 23.

EXAMPLE 111

2-Amino-N-benzyl-3-bromo-N,5-dimethyl-benzylamine and its hydrochloride, m.p. 220–222° C, were prepared from 2-amino-3-bromo-5-methyl-benzyl alcohol, thionyl chloride and N-methyl-benzylamine analogous to Example 1.

EXAMPLE 112

N-(2-Acetamino-3-bromo-5-methyl-benzyl)-pyrrolidine and its hydrochloride, m.p. 197–198° C, were prepared from N-(2-amino-3-bromo-5-methyl-benzyl)-pyrrolidine and acetic acid anhydride analogous to Example 23.

EXAMPLE 113

N-(2-Amino-3-bromo-5-methyl-benzyl)-pyrrolidine and its hydrochloride, m.p. 179–181° C, were prepared from 2-amino-3-bromo-5-methyl-benzyl alcohol, thionyl chloride and pyrrolidine analogous to Example 1.

EXAMPLE 114

N-(2-Acetamino-3-bromo-5-methyl-benzyl)-piperidine and its hydrochloride, m.p. 252–253° C, were prepared from N-(2-amino-3-bromo-5-methyl-benzyl)-piperidine and acetic acid anhydride analogous to Example 23.

EXAMPLE 115

N-(2-Amino-3-bromo-5-methyl-benzyl)-piperidine and its hydrochloride, m.p. 238–239° C, were prepared from 2-amino-3-bromo-5-methyl-benzyl alcohol, thionyl chloride and piperidine analogous to Example 1.

EXAMPLE 116

N-(2-Amino-3-bromo-5-methyl-benzyl)-morpholine and its hydrochloride, m.p. 243–244° C, were prepared from 2-amino-3-bromo-5-methyl-benzyl alcohol, thionyl chloride and morpholine analogous to Example 1.

EXAMPLE 117

N-(2-Acetamino-5-methyl-benzyl)-hexamethyleneamine and its hydrochloride, m.p. 164–165° C, were prepared from 2-acetamino-5-methyl-benzyl bromide and hexamethyleneamine analogous to Example 6.

EXAMPLE 118

N-(2-Amino-5-methyl-benzyl)-hexamethyleneamine and its dihydrochloride, m.p. 205–207° C, were prepared by hydrolysis of N-(2-acetamino-5-methyl-benzyl)-hexamethyleneamine in hydrochloric acid analogous to Example 34.

EXAMPLE 119

N-(2-Amino-3-bromo-5-methyl-benzyl)-hexamethylemeamine and its hydrochloride, m.p. 193–194° C, were prepared from 2-amino-3-bromo-5-methyl-benzyl-alcohol, thionyl chloride and hexamethyleneamine analogous to Example 1.

EXAMPLE 120

2-Amino-3-bromo-N,N-dimethyl-5-methoxy-benzylamine was prepared from 2-amino-N,N-dimethyl-5-methoxy-benzylamine and bromine analogous to Example 9. Proof of structure by IR-, UV- and NMR-spectra, IR-spectrum (methylenechloride): 3250 $cm^{-1}$ $NH_2$; 3410 $cm^{-1}$ $NH_2$; 2780 $cm^{-1}$ $N(CH_3)_2$; 2830 $cm^{-1}$ $OCH_3$; 1590 $cm^{-1}$ C=C; 1600 $cm^{-1}$ C=C.

EXAMPLE 121

2-Amino-N,N-dimethyl-5-methoxy-benzylamine was prepared from 2-amino-5-methoxy-benzyl alcohol, thionyl chloride and dimethylamine analogous to Example 1. Proof of structure by IR-, UV- and NMR-spectra. IR-spectrum (methylenechloride): 3280 $cm^{-1}$ $NH_2$; 3420 $cm^{-1}$ $NH_2$; 2780 $cm^{-1}$ $N(CH_3)_2$; 2830 $cm^{-1}$ $OCH_3$; 1600 $cm^{-1}$ C=C.

EXAMPLE 122

2-Amino-N,N-diethyl-5-methoxy-benzylamine was prepared from 2-amino-5-methoxy-benzyl alcohol, thionyl chloride and diethylamine analogous to Example 1. Proof of structure by IR-, UV- and NMR-spectra. IR-spectrum (methylenechloride): 3260 $cm^{-1}$ $NH_2$; 3410 $cm^{-1}$ $NH_2$; 2830 $cm^{-1}$ $OCH_3$; 2800 $cm^{-1}$ N-ethyl; 1510 $cm^{-1}$ C=C; 1600 $cm^{-1}$ C=C.

EXAMPLE 123

2-Amino-3-bromo-N,N-diethyl-5-methoxy-benzylamine was prepared from 2-amino-N,N-diethyl-5-methoxy-benzylamine and bromine analogous to Example 9. Proof of structure by IR-, UV- and NMR-spectra. IR-spectrum (methylenechloride): 3250 $cm^{-1}$ $NH_2$; 3410 $cm^{-1}$ $NH_2$; 2830 $cm^{-1}$ $OCH_3$; 2800 $cm^{-1}$ N-ethyl; 1480 $cm^{-1}$ C=C; 1590 $cm^{-1}$ C=C.

EXAMPLE 124

N-(2-Amino-3-bromo-5-methoxy-benzyl)-morpholine was prepared from N-(2-amino-5-methoxy-benzyl)-morpholine and bromine analogous to Example 9. Proof of structure by IR-, UV- and NMR-spectra, IR-spectrum (methylenechloride): 3280 $cm^{-1}$ $NH_2$; 3420 $cm^{-1}$ $NH_2$; 2830 $cm^{-1}$ $OCH_3$; 2810 $cm^{-1}$ N-alkyl; 1480 $cm^{-1}$ C=C; 1590 $cm^{-1}$ C=C.

EXAMPLE 125

2-Amino-3-bromo-N-cyclohexyl-5-methoxy-N-methyl-benzylamine was prepared from 2-amino-N-cyclohexyl-5-methoxy-N-methyl-benzylamine and bromine analogous to Example 9. Proof of structure by IR- and UV-spectra. IR-spectrum (methylenechloride): 3240 $cm^{-1}$ $NH_2$; 3410 $cm^{-1}$ $NH_2$; 2860 $cm^{-1}$ aliphatic hydrocarbon; 2940 $cm^{-1}$ aliphatic hydrocarbon; 2830 $cm^{-1}$ $OCH_3$; 2800 $cm^{-1}$ N-alkyl; 1480 $cm^{-1}$ C=C; 1590 $cm^{-1}$ C=C.

EXAMPLE 126

2-Amino-3-bromo-N-cyclohexyl-N-ethyl-5-methoxy-benzylamine was prepared from 2-amino-N-cyclohexyl-N-ethyl-5-methoxy-benzylamine and bromine analogous to Example 9. Proof of structure by IR-, UV- and NMR-spectra. IR-spectrum (methylenechloride): 3240 $cm^{-1}$ $NH_2$; 3410 $cm^{-1}$ $NH_2$; 2860 $cm^{-1}$ aliphatic hydrocarbon; 2940 $cm^{-1}$ aliphatic hydrocarbon; 2830 $cm^{-1}$ $OCH_3$; 2800 $cm^{-1}$ N-ethyl (shoulder); 1480 $cm^{-1}$ C=C; 1590 $cm^{-1}$ C=C.

EXAMPLE 127

N-(2-Amino-5-methoxy-benzyl)-morpholine was prepared from 2-amino-5-methoxy-benzyl alcohol, thionyl chloride and morpholine analogous to Example 1. Proof of structure by IR- and UV-spectra. IR-spectrum (methylenechloride) 3280 $cm^{-1}$ $NH_2$; 3410 $cm^{-1}$ $NH_2$; 2830 $cm^{-1}$ $OCH_3$; 2800 $cm^{-1}$ N-alkyl; 1500 $cm^{-1}$ C=C; 1600 $cm^{-1}$ C=C.

EXAMPLE 128

2-Amino-N-cyclohexyl-5-methoxy-N-methyl-benzylamine was prepared from 2-amino-5-methoxy-benzyl alcohol, thionyl chloride and N-methyl-cyclohexylamine analogous to Example 1. Proof of structure by IR- and UV-spectra. IR-spectrum (methylenechloride): 3240 $cm^{-1}$ $NH_2$; 3400 $cm^{-1}$ $NH_2$; 2780 $cm^{-1}$ N-methyl; 2830 $cm^{-1}$ $OCH_3$; 2850 $cm^{-1}$ aliphatic hydrocarbon; 2930 $cm^{-1}$ aliphatic hydrocarbon; 1500 $cm^{-1}$ C=C; 1510 $cm^{-1}$ C=C.

EXAMPLE 129

2-Amino-N-cyclohexyl-N-ethyl-5-methoxy-benzylamine was prepared from 2-amino-5-methoxy-benzyl alcohol, thionyl chlorie and N-ethyl-cyclohexylamine analogous to Example 1. Proof of structure by IR- and UV-spectra. IR-spectrum (methylenechloride): 3250 $cm^{-1}$ $NH_2$; 3400 $cm^{-1}$ $NH_2$; 2830 $cm^{-1}$ $OCH_3$; 2800 $cm^{-1}$ N-ethyl (shoulder); 2850 $cm^{-1}$ aliphatic hydrocarbon; 2930 $cm^{-1}$ aliphatic hydrocarbon; 1500 $cm^{-1}$ C=C; 1600 $cm^{-1}$ C=C.

EXAMPLE 130

N-(2-Amino-3-bromo-5-methoxy-benzyl)-piperidine was prepared from N-(2-amino-5-methoxy-benzyl)-piperidine and bromine analogous to Example 9. Proof of structure by IR-, UV- and NMR-spectra. IR-spectrum (methylenechloride): 3240 $cm^{-1}$ $NH_2$; 3400 $cm^{-1}$ $NH_2$; 2830 $cm^{-1}$ $OCH_3$; 2790 $cm^{-1}$ N-alkyl; 1480 $cm^{-1}$ C=C; 1590 $cm^{-1}$ C=C.

EXAMPLE 131

N-(2-Amino-5-methoxy-benzyl)-piperidine was prepared from 2-amino-5-methoxy-benzyl alcohol, thionyl chloride and piperidine analogous to Example 1. Proof of structure by IR- and UV-spectra. IR-spectrum (methylene-chloride): 3260 $cm^{-1}$ $NH_2$; 3410 $cm^{-1}$ $NH_2$; 2830 $cm^{-1}$ $OCH_3$; 2800 $cm^{-1}$ N-alkyl; 1510 $cm^{-1}$ C=C; 1600 $cm^{-1}$ C=C.

EXAMPLE 132

2-Amino-5-bromo-N-cyclohexyl-3-methoxy-N-methyl-benzylamine and its hydrochloride, m.p. 198–201° C, were prepared from 2-amino-N-cyclohexyl-3-methoxy-N-methyl-benzylamine and bromine analogous to Example 9.

EXAMPLE 133

4-Amino-3-bromo-N-cyclohexyl-5-methoxy-N-methyl-benzylamine and its hydrochloride, m.p. 177–180° C, were prepared from 4-amino-N-cyclohexyl-5-methoxy-N-methyl-benzylamine and bromine analogous to Example 9.

EXAMPLE 134

N-(2-Amino-5-fluoro-benzyl)-hexamethyleneamine, b.p. 96–100° C at 0.03 mm Hg, was prepared from 2-amino-5-fluoro-N-hexamethyleneamino-benzamide and lithium and aluminum hydride analogous to Example 35.

EXAMPLE 135

N-(2-Amino-3-bromo-5-fluoro-benzyl)-hexamethyleneamine and its hydrochloride, m.p. 197–199° C, were prepared from N-(2-amino-5-fluoro-benzyl)-hexamethyleneamine and bromine analogous to Example 9.

EXAMPLE 136

N-(2-Amino-3-bromo-5-fluoro-benzyl)-morpholine and its hydrochloride, m.p. 230–232° C, were prepared from N-(2-amino-5-fluoro-benzyl)-morpholine and bromine analogous to Example 9.

EXAMPLE 137

2-Amino-3-bromo-N,N-diethyl-5-fluoro-benzylamine and its hydrochloride, m.p. 182–184° C, were prepared from 2-amino-3-bromo-5-fluoro-benzyl alcohol, thionyl chloride and diethylamine analogous to Example 1.

EXAMPLE 138

2-Amino-3-bromo-N-cyclohexyl-N-ethyl-5-fluoro-benzylamine and its hydrochloride, m.p. 176–178° C, were prepared from 2-amino-3-bromo-5-fluoro-benzyl alcohol, thionyl chloride and N-ethyl-cyclohexylamine analogous to Example 1.

EXAMPLE 139

2-Amino-3-bromo-N-ethyl-5-fluoro-benzylamine and its hydrochloride, m.p. 210–212° C, were prepared from 2-amino-3-bromo-5-fluoro-benzyl alcohol, thionyl chloride and ethylamine analogous to Example 1.

EXAMPLE 140

2-Amino-3-bromo-N,N-dimethyl-5-fluoro-benzylamine and its hydrochloride, m.p. 241–243° C, were prepared from 2-amino-3-bromo-5-fluoro-benzyl alcohol, thionyl chloride and dimethylamine analogous to Example 1.

EXAMPLE 141

2-Amino-3-N-cyclohexyl-5-fluoro-benzylamine and its hydrochloride, m.p. 250–252° C (decomp.), were prepared from 2-amino-3-bromo-5-fluoro-benzyl alcohol, thionyl chloride and cyclohexylamine analogous to Example 1.

EXAMPLE 142

2-Amino-3-bromo-5-fluoro-N-methyl-benzylamine and its hydrochloride, m.p. 215–217° C (decomp.), were prepared from 2-amino-3-bromo-5-fluoro-benzyl alcohol, thionyl chloride and methylamine analogous to Example 1.

EXAMPLE 143

2-Acetamino-5-bromo-N-cyclohexyl-N-methyl-3-[(N-methyl-cyclohexylamino)-methyl]-benzylamine, m.p. 194–199° C, was prepared from 2-acetylamino-5-bromo-3-bromomethyl-benzyl bromide and N-methyl-cyclohexylamine analogous to Example 3.

EXAMPLE 144

2-Acetylamino-5-bromo-N-(trans-4'-hydroxy-cyclohexyl)-N-methyl-3-[(N-methyl-trans-4''-hydroxy-cyclohexylamino)-methyl]-benzylamine, m.p. 208–209° C, was prepared from 2-acetylamino-5-bromo-3-bromomethyl-benzyl bromide and trans-4-methylamino-cyclohexanol analogous to Example 3.

EXAMPLE 145

2-Amino-N,N-diethyl-3-(diethylamino-methyl)-benzylamine and its dihydrochloride, m.p. 199–201° (decomp.), were prepared by hydrolysis of 2-acetamino-N,N-diethyl-3-(diethylamino-methyl)-benzylamine in 2 N hydrochloric acid analogous to Example 14.

EXAMPLE 146

2-Amino-5-bromo-N-(trans-4'-hydroxy-cyclohexyl)-N-methyl-3-[(N-methyl-trans-4''-hydroxy-cyclohexylamino)-methyl]-benzylamine, m.p. 179–180° C, was prepared by hydrolysis of 2-acetamino-5-bromo-N-(trans-4'-hydroxy-cyclohexyl)-N-methyl-3-[(N-methyl-trans-4''-hydroxy-cyclohexylamino)-methyl]-benzylamine in 2 N hydrochloric acid analogous to Example 14.

EXAMPLE 147

2-Acetylamino-N,N,3-trimethyl-benzylamine and its hydrochloride, m.p. 162–164° C, were prepared from 2-acetylamino-3-methyl-benzyl bromide and dimethylamine analogous to Example 2.

EXAMPLE 148

2-Acetamino-N,3-dimethyl-N-ethyl-benzylamine and its hydrochloride, m.p. 168–170° C, were prepared from 2-acetamino-3-methyl-benzyl bromide and N-methyl-ethylamine analogous to Example 2.

EXAMPLE 149

2-Acetamino-N,N-di-n-propyl-3-methyl-benzylamine and its hydrochloride, m.p. 156–159° C, were prepared from 2-acetamino-3-methyl-benzyl bromide and di-n-propylamine analogous to Example 2.

EXAMPLE 150

2-Acetamino-5-bromo-N,N,3-trimethyl-benzylamine, m.p. 114–116° C, was prepared from 2-acetamino-5-bromo-3-methyl-benzyl bromide and dimethylamine analogous to Example 2.

EXAMPLE 151

2-Acetamino-N-ethyl-5-bromo-N,3-dimethyl-benzylamine, m.p. 81–83° C, was prepared from 2-acetamino-5-bromo-3-methyl-benzyl bromide and N-methyl-ethylamine analogous to Example 2.

EXAMPLE 152

2-Acetamino-5-bromo-N,N-diethyl-3-methyl-benzylamine and its hydrochloride, m.p. 192.5–194° C, were prepared from 2-acetamino-5-bromo-3-methyl-benzyl bromide and diethylamine analogous to Example 2.

EXAMPLE 153

N-(2-Acetamino-5-bromo-3-methyl-benzyl)-pyrrolidine, m.p. 123–127° C, was prepared from 2-acetamino-5-bromo-3-methyl-benzyl bromide and pyrrolidine analogous to Example 2.

EXAMPLE 154

N-(2-Acetamino-5-bromo-3-methyl-benzyl)-piperidine, m.p. 119–124° C, was prepared from 2-acetamino-5-bromo-3-methyl benzyl bromide and piperidine analogous to Example 2.

EXAMPLE 155

N-(2-Acetamino-5-bromo-3-methyl-benzyl)-hexamethyleneamine, m.p. 129–132° C, was prepared from 2-acetamino-5-bromo-3-methyl-benzyl bromide and hexamethyleneamine analogous to Example 2.

EXAMPLE 156

N-(2-Acetamino-5-bromo-3-methyl-benzyl)-morpholine, m.p. 105–110° C, was prepared from 2-acetamino-5-bromo-3-methyl-benzyl bromide and morpholine analogous to Example 2.

EXAMPLE 157

2-Acetamino-5-bromo-N-cyclohexyl-N,3-dimethyl-benzylamine m.p. 102–104° C, was prepared from 2-acetamino-5-bromo-3-methyl-benzyl bromide and N-methyl-cyclohexylamine analogous to Example 2.

EXAMPLE 158

2-Acetamino-5-bromo-N,3-dimethyl-N-(cis-3'-hydroxy-cyclohexyl)-benzylamine, m.p. 144–146° C, was prepared from 2-acetamino-5-bromo-3-methyl-benzyl bromide and cis-3-methylamino-cyclohexanol analogous to Example 2.

EXAMPLE 159

2-Acetamino-5-bromo-N,3-dimethyl-N-(trans-4'-hydroxy-cyclohexyl)-benzylamine, m.p. 136.5–138° C, was prepared from 2-acetamino-5-bromo-3-methyl-benzyl bromide and trans-4-methylamino-cyclohexanol analogous to Example 2.

EXAMPLE 160

2-Acetamino-5-bromo-N-cyclohexyl-N-ethyl-3-methyl-benzylamine, m.p. 115–119° C, was prepared from 2-acetamino-5-bromo-3-methyl-benzyl bromide and N-ethyl-cyclohexylamine analogous to Example 2.

EXAMPLE 161

2-Acetamino-5-bromo-N-(trans-4-hydroxy-cyclohexyl)-N-ethyl-3-methyl-benzylamine, m.p. 168–170° C, was prepared from 2-acetamino-5-bromo-3-methyl-benzyl bromide and trans-4-ethylamino-cyclohexanol analogous to Example 2.

EXAMPLE 162

2-Acetamino-N-benzyl-5-bromo-N,3-dimethyl-benzylamine, m.p. 97–99° C, was prepared from 2-acetamino-5-bromo-3-methyl-benzyl bromide and N-methyl-benzylamine analogous to Example 2.

EXAMPLE 163

N-(2-Acetamino-5-bromo-3-methyl-benzyl)-N'-methyl-piperazine and its dihydrochloride, m.p. 256–257° C (decomp.), were prepared from 2-acetamino-5-bromo-3-methyl-benzyl bromide and N-methyl-piperazine analogous to Example 2.

EXAMPLE 164

2-Amino-N,N,3-trimethyl-benzylamine and its dihydrochloride, m.p. 188–190° C, were prepared by hydrolysis of 2-acetamino-N,N,3-trimethyl-benzylamine in 2 N hydrochloric acid analogous to Example 13.

EXAMPLE 165

2-Amino-N,3-dimethyl-N-ethyl-benzylamine and its dihydrochloride, m.p. 196–198° C (decomp.), were prepared by hydrolysis of 2-acetamino-N,3-dimethyl-N-ethyl-benzylamine in 2 N hydrochloric acid analogous to Example 13.

EXAMPLE 166

2-Amino-N,N-di-n-propyl-3-methyl-benzylamine and its dihydrochloride, m.p. 168–173° C (decomp,), were prepared by hydrolysis of 2-acetamino-N,N-di-n-propyl-3-methyl -benzylamine in 2 N hydrochloric acid analogous to Example 13.

EXAMPLE 167

2-Amino-5-bromo-N,N,3-trimethyl-benzylamine and its hydrochloride, m.p. 218–221° C (decomp.), were prepared by hydrolysis of 2-acetamino-5-bromo-N,N,3-trimethyl-benzylamine in 2 N hydrochloric acid analogous to Example 13.

EXAMPLE 168

2-Amino-5-bromo-N,3-dimethyl-N-ethyl-benzylamine and its hydrochloride, m.p. 191–193° C (decomp.), were prepared by hydrolysis of 2-acetamino-5-bromo-N,3-dimethyl-N-ethyl-benzylamine in 2 N hydrochloric acid analogous to Example 13.

EXAMPLE 169

2-Amino-5-bromo-N,N,-diethyl-3-methyl-benzylamine and its hydrochloride, m.p. 177–179° C (decomp.), were prepared from 2-amino-N,N-diethyl-3-methyl-benzylamine hydrochloride and bromine analogous to Example 10.

EXAMPLE 170

N-(2-Amino-5-bromo-3-methyl-benzyl)-pyrrolidone and its dihydrochloride, m.p. 206–210° C (decomp.), were prepared by hydrolysis of N-(2-acetamino-5-bromo-3-methyl-benzyl)-pyrrolidine and 2 N hydrochloric acid analogous to Example 13.

EXAMPLE 171

N-(2-Amino-5-bromo-3-methyl-benzyl)-piperidine and its dihydrochloride, m.p. 176–179° C (decomp.), were prepared by hydrolysis of N-(2-acetamino-5-bromo-3-methyl-benzyl)-piperidine and 2 N hydrochloric acid analogous to Example 13.

EXAMPLE 172

N-(2-Amino-5-bromo-3-methyl-benzyl)-hexamethyleneamine and its dihydrochloride, m.p. 159–164° C (decomp.), were prepared by hydrolysis of N-(2-acetamino-5-bromo-3-methyl-benzyl)-hexamethyleneamine in 2 N hydrochloric acid analogous to Example 13.

EXAMPLE 173

N-(2-Amino-5-bromo-3-methyl-benzyl)-morpholine and its dihydrochloride, m.p. 159–163° C (decomp.), were prepared by hydrolysis of N-(2-acetamino-5-bromo-3-methyl-benzyl)-morpholine in 2 N hydrochloric acid analogous to Example 13.

EXAMPLE 174

2-Amino-5-bromo-N-(trans-4'-hydroxy-cyclohexyl)-3-methyl-benzylamine and its hydrochloride, m.p. 225–226° C (decomp.), were prepared by hydrolysis of 2-acetamino-5-bromo-N-(trans-4'-hydroxy-cyclohexyl)-3-methyl-benzylamine in 2 N hydrochloric acid analogous to Example 13.

EXAMPLE 175

2-Amino-5-bromo-N-cyclohexyl-N,3-dimethyl-benzylamine and its hydrochloride, m.p. 206.5–207.5° C (decomp.), were prepared by hydrolysis of 2-acetamino-5-bromo-N-cyclohexyl-N,3-dimethyl-benzylamine in 2 N hydrochloric acid analogous to Example 13.

EXAMPLE 176

2-Amino-5-bromo-N,3-dimethyl-N-(cis-3'-hydroxy-cyclohexyl)benzylamine, m.p. 118–119° C, was prepared by hydrolysis of 2-acetamino-5-bromo-N,3-dimethyl-N-(cis-3'-hydroxy-cyclohexyl)-benzylamine, m.p. 118–119° C, was prepared by hydrolysis of 2-acetamino-5-bromo-N,3-dimethyl-N-(cis-3'-hydroxy-cyclohexyl)-benzylamine in 2N hydrochloric acid analogous to Example 13.

EXAMPLE 177

2-Amino-5-bromo-N,3-dimethyl-N-(trans-4'-hydroxy-cyclohexyl)-benzylamine, m.p. 122–123.5° C, was prepared by hydrolysis of 2-acetamino-5-bromo-N,3-dimethyl-N-(trans-4'-hydroxy-cyclohexyl)-benzylamine in 2 N hydrochloric acid analogous to Example 13.

EXAMPLE 178

2-Amino-5-bromo-N-cyclohexyl-N-ethyl-3-methyl-benzylamine and its dihydrochloride, m.p. 183–187° C (decomp.), were prepared by hydrolysis of 2-acetamino-5-bromo-N-cyclohexyl-N-ethyl-3-methyl-benzylamine in 2 N hydrochloric acid analogous to Example 13.

EXAMPLE 179

2-Amino-5-bromo-N-(trans-4'-hydroxy-cyclohexyl)-N-ethyl-3-methyl-benzylamine and its hydrochloride, m.p. 156–161° C (decomp.), were prepared by hydrolysis of 2-acetamino-5-bromo-N-(trans-4'-hydroxy-cyclohexyl)-N-ethyl-3-methyl-benzylamine in 2 N hydrochloric acid analogous to Example 13.

EXAMPLE 180

2-Amino-N-benzyl-5-bromo-N,3-dimethyl-benzylamine and its hydrochloride, m.p. 214–216° C (decomp.), were prepared by hydrolysis of 2-acetamino-N-benzyl-5-bromo-N,3-dimethyl-benzylamine in 2 N hydrochloric acid analogous to Example 13.

EXAMPLE 181

2-Acetamino-4-tert.butyl-N-cyclohexyl-N-methyl-benzylamine and its hydrochloride, m.p. 231–234° C, were prepared from 2-acetamino-4-tert.butyl-benzyl bromide and N-methyl-cyclohexylamine analogous to Example 4.

EXAMPLE 182

2-Acetamino-5-bromo-4-tert.-butyl-N,N-dimethyl-benzylamine, m.p. 111–113° C, was prepared from 2-acetamino-5-bromo-4-tert.butyl-benzyl bromide and dimethylamine analogous to Example 4.

EXAMPLE 183

2-Acetamino-5-bromo-4-tert.butyl-N,N-diethyl-benzylamine, m.p. 88–91° C, was prepared from 2-acetamino-5-bromo-4-tert.butyl-benzyl bromide and diethylamine analogous to Example 4.

EXAMPLE 184

2-Acetamino-5-bromo-4-tert.butyl-N-(hydroxy-tert-.butyl)-benzylamine, m.p. 125–127° C, was prepared from 2-acetamino-5-bromo-4-tert.butyl-benzyl bromide and hydroxy-tert.butylamine analogous to Example 4.

EXAMPLE 185

N-(2-Acetamino-5-bromo-4-tert.butyl-benzyl)-pyrrolidine, m.p. 103–107° C, was prepared from 2-acetamino-5-bromo-4-tert.butyl-benzyl bromide and pyrrolidine analogous to Example 4.

EXAMPLE 186

N-(2-Acetamino-5-bromo-4-tert.butyl-benzyl)-piperidine, m.p. 132–134° C, was prepared from 2-acetamino-5-bromo-4-tert.butyl-benzyl bromide and piperidine analogous to Example 4.

EXAMPLE 187

N-(2-Acetamino-5-bromo-4-tert.butyl-benzyl)-morpholine, m.p. 136–139° C, was prepared from 2-acetamino-5-bromo-4-tert.butyl-benzyl bromide and morpholine analogous to Example 4.

EXAMPLE 188

2-Acetamino-5-bromo-4-tert.butyl-N-(cis-3'-hydroxy-cyclohexyl)-N-methyl-benzylamine, m.p. 167–172° C, was prepared from 2-acetamino-5-bromo-4-tert.butyl-benzyl bromide and cis-3-methylamino-cyclohexanol analogous to Example 4.

EXAMPLE 189

2-Acetamino-5-bromo-4-tert.butyl-N-(trans-4'-hydroxy-cyclohexyl)-N-methyl-benzylamine, m.p. 174–176° C, was prepared from 2-acetamino-5-bromo-4-tert.butyl-benzyl bromide and trans-4-methylamino-cyclohexanol analogous to Example 4.

EXAMPLE 190

2-Acetamino-5-bromo-4-tert.butyl-N-cyclohexyl-N-ethyl-benzylamine, m.p. 102–105° C, was prepared from 2-acetamino-5-bromo-4-tert.butyl-benzyl bromide and N-ethyl-cyclohexyl-amine analogous to Example 4.

EXAMPLE 191

N-(2-Acetamino-5-bromo-4-tert.butyl-benzyl)-N'-methyl-piperazine and its dihydrochloride, m.p. >250° C (decomp.), were prepared from 2-acetamino-5-bromo-4-tert.butyl-benzyl bromide and N-methyl piperazine analogous to Example 4.

EXAMPLE 192

N-(2-Acetamino-5-bromo-4-tert.butyl-benzyl)-camphidine, m.p. 133–138° C, was prepared from 2-acetamino-5-bromo-4-tert.butyl-benzyl bromide and camphidine analogous to Example 4.

EXAMPLE 193

2-Amino-4-tert.butyl-N,N-diethyl-benzylamine and its dihydrochloride, m.p. 188–190° C, were prepared by hydrolysis of 2-acetamino-4-tert.butyl-N,N-diethyl-benzylamine in aqueous-ethanolic hydrochloric acid analogous to Example 15.

EXAMPLE 194

2-Amino-4-tert.butyl-N-cyclohexyl-N-methyl-benzylamine and its hydrochloride, m.p. 198–199° C, were prepared by hydrolysis of 2-acetamino-4-tert.butyl-N-cyclohexyl-N-methyl-benzylamine in 3 N hydrochloric acid analogous to Example 15.

EXAMPLE 195

2-Amino-5-bromo-4-tert.butyl-N,N-dimethyl-benzylamine and its dihydrochloride, m.p. 213–218° C (decomp.), were prepared by hydrolysis of 2-acetamino-5-bromo-4-tert.butyl-N,N-dimethyl-benzylamine in 3 N hydrochloric acid analogous to Example 15.

EXAMPLE 196

2-Amino-5-bromo-4-tert.butyl-N,N-diethyl-benzylamine and its hydrochloride, m.p. 198–200° C (decomp.), were prepared by hydrolysis of 2-acetamino-5-bromo-4-tert.butyl-N,N-diethyl-benzylamine in 3 N hydrochloric acid analogous to Example 15.

EXAMPLE 197

2-Amino-5-bromo-4-tert.butyl-N,N-diallyl-benzylamine and its hydrochloride, m.p. 176–178° C, were prepared by hydrolysis of 2-acetamino-5-bromo-4-tert.butyl-N,N-diallyl-benzylamine in 3 N hydrochloric acid analogous to Example 15.

EXAMPLE 198

2-Amino-5-bromo-4-tert.butyl-N-(hydroxy-tert.butyl)-benzylamine, m.p. 123–125° C, was prepared by hydrolysis of 2-acetamino-5-bromo-4-tert.butyl-N-(hydroxy-tert.butyl)-benzylamine in 3 N hydrochloric acid analogous to Example 15.

EXAMPLE 199

2-Amino-5-bromo-4-tert.butyl-N-(1',3'-dihydroxy-2'-methyl-propyl-2')-benzylamine and its dihydrochloride, m.p. 200–205° C (decomp.), were prepared by hydrolysis of 2-acetamino-5-bromo-4-tert.butyl-N-(1',3'-dihydroxy-2'-methyl-propyl-2')-benzylamine in 4 N hydrochloric acid analogous to Example 15.

EXAMPLE 200

2-Amino-5-bromo-4-tert.butyl-N-(tris-hydroxymethyl-methyl)-benzylamine and its dihydrochloride, m.p. >190° C (decomp.), were prepared by hydrolysis of 2-acetamino-5-bromo-4-tert.butyl-N-(tris-hydroxymethyl-methyl)-benzylamine in 4 N hydrochloric acid analogous to Example 15.

EXAMPLE 201

N-(2-Amino-5-bromo-4-tert.butyl-benzyl)-pyrrolidine and its hydrochloride, m.p. >190° C (decomp.), were prepared by hydrolysis of N-(2-acetamino-5-bromo-4-tert.butyl-benzyl)-pyrrolidine in 3 N hydrochloric acid analogous to Example 15.

EXAMPLE 202

N-(2-Amino-5-bromo-4-tert.butyl-benzyl)-piperidine and is dihydrochloride, m.p. 188–195° C, were prepared by hydrolysis of N-(2-acetamino-5-bromo-4-tert.butyl-benzyl)-piperidine in 3 N hydrochloric acid analogous to Example 15.

EXAMPLE 203

N-(2-Amino-5-bromo-4-tert.butyl-benzyl)-morpholine and its dihydrochloride, m.p. 194–198° C (decomp.), were prepared by hydrolysis of N-(2-acetamino-5-bromo-4-tert.butyl-benzyl)-morpholine in 3 N hydrochloric acid analogous to Example 15.

EXAMPLE 204

2-Amino-5-bromo-4-tert.butyl-N-(trans-4'-hydroxy-cyclohexyl)-benzylamine and its dihydrochloride, m.p. 212–218° C (decomp.), were prepared by hydrolysis of 2-acetamino-5-bromo-4-tert.butyl-N-(trans-4'-hydroxy-cyclohexyl)-benzylamine in 4 N hydrochloric acid analogous to Example 15.

EXAMPLE 205

2-Amino-5-bromo-4-tert.butyl-N-(cis-3'-hydroxy-cyclohexyl)-N-methyl-benzylamine and its dihydrochloride, m.p. 205–208° C (decomp.), were prepared by hydrolysis of 2-acetamino-5-bromo-4-tert.butyl-N-(cis-3'-hydroxy-cyclohexyl)-N-methyl-benzylamine in 4 N hydrochloric acid analogous to Example 15.

EXAMPLE 206

2-Amino-5-bromo-4-tert.butyl-N-(trans-4'-hydroxy-cyclohexyl)-N-methyl-benzylamine and its hydrochloride, m.p. 208–210° C (decomp.), were prepared by hydrolysis of 2-acetamino-5-bromo-4-tert.butyl-N-(trans-4'-hydroxy-cyclohexyl)-N-methyl-benzylamine in 3 N hydrochloric acid analogous to Example 15.

EXAMPLE 207

2-Amino-5-bromo-4-tert.butyl-N-cyclohexyl-N-ethyl-benzylamine and its hydrochloride, m.p. 191–194° C (decomp.), were prepared by hydrolysis of 2-acetamino-5-bromo-4-tert.butyl-N-cyclohexyl-N-ethyl-benzylamine in aqueous-ethanolic hydrochloric acid analogous to Example 15.

EXAMPLE 208

N-(2-Amino-5-bromo-4-tert.butyl-benzyl)-N'-methyl-piperazine and its trihydrochloride, m.p. 170–180° C (decomp.), were prepared by hydrolysis of N-(2-acetamino-5-bromo-4-tert.butyl-benzyl)-N'-methyl-piperazine in 3 N hydrochloric acid analogous to Example 15.

EXAMPLE 209

N-(2-Amino-5-bromo-4-tert.butyl-benzyl)-camphidine and its dihydrochloride, m.p. 198–205° C (decomp.), were prepared by hydrolysis of N-(2-acetamino-5-bromo-4-tert.butyl-benzyl)-camphidine in 3 N hydrochloric acid analogous to Example 15.

EXAMPLE 210

4-Amino-3-tert.butyl-N,N-diethyl-benzylamine and its dihydrochloride, m.p. 183–185° C (decomp.), were prepared by hydrolysis of 4-acetamino-3-tert.butyl-N,N-diethyl-benzylamine in 3 N hydrochloric acid analogous to Example 17.

EXAMPLE 211

4-Amino-5-bromo-3-tert.butyl-N,N-diethyl-benzylamine and its dihydrochloride, m.p. 201–204° C (decomp.) were prepared from 4-amino-3-tert.butyl-N,N-diethyl-benzylamine dihydrochloride and bromine analogous to Example 10.

EXAMPLE 212

4-Amino-5-bromo-3-tert.butyl-N-cyclohexyl-methyl-benzylamine and its hydrochloride, m.p. 198–201° C (decomp.), were prepared from 4-amino-3-tert.butyl-N-cyclohexyl-N-methyl-benzylamine dihydrochloride and bromine analogous to Example 10.

EXAMPLE 213

5-Acetyl-2-acetamino-N,N-diethyl-benzylamine, m.p. 102–103° C, was prepared from 5-acetyl-2-acetamino-benzyl bromide and diethylamine analogous to Example 8.

EXAMPLE 214

5-Acetyl-2-acetamino-N,N-di-n-propyl-benzylamine, m.p. 80–82° C, was prepared from 5-acetyl-2-acetamino-benzyl bromide and di-n-propylamine analogous to Example 8.

EXAMPLE 215

5-Acetyl-2-acetamino-N,N-di-n-butyl-benzylamine, m.p. 40–42° C, was prepared from 5-acetyl-2-acetamino-benzyl bromide and di-n-butylamine analogous to Example 8.

EXAMPLE 216

N-(5-Acetyl-2-acetamino-benzyl)-pyrrolidine, m.p. 88–90° C, was prepared from 5-acetyl-2-acetamino-benzyl bromide and pyrrolidine analogous to Example 8.

EXAMPLE 217

N-(5-Acetyl-2-acetamino-benzyl)-piperidine and its hydrochloride, m.p. 210–212° C, were prepared from 5-acetyl-2-acetamino-benzyl bromide and piperidine analogous to Example 8.

EXAMPLE 218

N-(5-Acetyl-2-acetamino-benzyl)-hexamethyleneamine, m.p. 112–114° C, was prepared from 5-acetyl-2-acetamino-benzyl bromide and hexamethyleneamine analogous to Example 8.

EXAMPLE 219

N-(5-Acetyl-2-acetamino-benzyl)-morpholine, m.p. 100–102° C, was prepared from 5-acetyl-2-acetamino-benzyl bromide and morpholine analogous to Example 8.

EXAMPLE 220

5-Acetyl-2-acetamino-N-cyclohexyl-N-methyl-benzylamine and its hydrochloride, m.p. 210–211° C, were prepared from 5-acetyl-2-acetamino-benzyl bromide and N-methyl-cyclohexylamine analogous to Example 8.

EXAMPLE 221

5-Acetyl-2-acetamino-N-ethyl-N-cyclohexyl-benzylamine, m.p. 98–100° C was prepared from 5-acetyl-2-acetamino-benzyl bromide and N-ethyl-cyclohexylamine analogous to Example 8.

EXAMPLE 222

5-Acetyl-2-acetamino-N-cyclohexyl-N-isopropyl-benzylamine, m.p. 108–110° C, was prepared from 5-acetyl-2-acetamino-benzyl bromide and N-isopropyl-cyclohexylamine analogous to Example 8.

EXAMPLE 223

N-(5-Acetyl-2-acetamino-benzyl)-N'-methyl-piperazine and its dihydrochloride, m.p. >275° C (decomp.), were prepared from 5-acetyl-2-acetamino-benzyl bromide and N-methylpiperazine analogous to Example 8.

EXAMPLE 224

5-Acetyl-2-amino-N,N-diethyl-benzylamine and its hydrochloride, m.p. 218–221° C, were prepared by hydrolysis of 5-acetyl-2-acetamino-N,N-diethyl-benzylamine in aqueous-ethanolic sodium hydroxide analogous to Example 18.

EXAMPLE 225

5-Acetyl-2-amino-N,N-di-n-propyl-benzylamine and its hydrochloride, m.p. 171–173° C, were prepared by hydrolysis of 5-acetyl-2-acetamino-N,N-di-n-propyl-benzylamine in aqueous-ethanol sodium hydroxide analogous to Example 18.

EXAMPLE 226

5-Acetyl-2-amino-N,N-di-n-butyl-benzylamine and its hydrochloride, m.p. 110–120° C, were prepared by hydrolysis of 5-acetyl-2-acetamino-N,N-di-n-butyl-benzylamine in 4 N hydrochloric acid analogous to Example 16.

EXAMPLE 227

N-(5-Acetyl-2-amino-benzyl)-pyrrolidine and its hydrochloride, m.p. 203–205° C, were prepared by hydrolysis of N-(5-acetyl-2-acetamino-benzyl)-pyrrolidine in aqueous-ethanolic sodium hydroxide analogous to Example 18.

EXAMPLE 228

N-(5-Acetyl-2-amino-benzyl)-piperidine and its hydrochloride, m.p. 220–222° C, were prepared by hydrolysis of N-(5-acetate-2-acetamino-benzyl)-piperidine in aqueous-ethanolic sodium hydroxide analogous to Example 18.

EXAMPLE 229

N-(5-Acetyl-2-amino-benzyl)-hexamethyleneamine and its hydrochloride, m.p. 205–207° C (decomp.), were prepared by hydrolysis of N-(5-acetyl-2-acetamino-benzyl)-hexamethyleneamine in aqueous-ethanolic sodium hydroxide analogous to Example 18.

EXAMPLE 230

N-(5-Acetyl-2-amino-benzyl)-morpholine and its hydrochloride, m.p. 218–220° C (decomp.), were prepared by hydrolysis of N-(5-acetyl-2-acetamino-benzyl)-morpholine in aqueous-ethanolic sodium hydroxide analogous to Example 18.

EXAMPLE 231

5-Acetyl-2-amino-N-cyclohexyl-N-ethyl-benzylamine, m.p. 100–102° C, was prepared by hydrolysis of 5-acetyl-2-acetamino-N-cyclohexyl-N-ethyl-benzylamine in aqueous-ethanol sodium hydroxide analogous to Example 18.

EXAMPLE 232

N-(5-Acetyl-2-amino-benzyl)-N'-methyl-piperazine, m.p. 135–138° C, was prepared by hydrolysis of N-(5-acetyl-2-acetamino-benzyl)-N'-methyl-piperazine in aqueous-ethanolic sodium hydroxide analogous to Example 18.

EXAMPLE 233

5-Acetyl-2-amino-3-bromo-N,N-diethyl-benzylamine and it hydrochloride, m.p. 208–212° C, were prepared from 5-acetyl-2-amino-N,N-diethyl-benzylamine hydrochloride and bromine analogous to Example 11.

EXAMPLE 234

5-Acetyl-2-amino-3-bromo-N,N-di-n-propyl-benzylamine and its hydrochloride, m.p. 136–140° C, were prepared from 5-acetyl-2-amino-N,N-di-n-propyl-benzylamine hydrochloride and bromine analogous to Example 11.

EXAMPLE 235

5-Acetyl-2-amino-3-bromo-N,N-di-n-butyl-benzylamine and its hydrochloride, m.p. 112–115° C, were prepared from 5-acetyl-2-amino-N,N-dibutyl-benzylamine hydrochloride and bromine analogous to Example 11.

EXAMPLE 236

N-(5-Acetyl-2-amino-3-bromo-benzyl)-pyrrolidine and its hydrochloride, m.p. 165–167° C, were prepared from N-(5-acetyl-2-amino-benzyl)-pyrrolidine hydrochloride and bromine analogous to Example 11.

EXAMPLE 237

N-(5-Acetyl-2-amino-3-bromo-benzyl)-piperidine, m.p. 108–110° C, was prepared from N-(5-acetyl-2-amino-benzyl)-piperidine hydrochloride and bromine analogous to Example 11.

EXAMPLE 238

N-(5-Acetyl-2-amino-3-bromo-benzyl)-hexamethyleneamine and its hydrochloride, m.p. 203–206° C, were prepared from N-(5-acetyl-2-amino-benzyl)-hexamethyleneamine hydrochloride and bromine analogous to Example 11.

EXAMPLE 239

N-(5-Acetyl-2-amino-3-bromo-benzyl)-morpholine and its hydrochloride, m.p. 235–239° C (decomp.), were prepared from N-(5-acetyl-2-amino-benzyl)-morpholine hydrochloride and bromine analogous to Example 11.

EXAMPLE 240

5-Acetyl-2-amino-3-bromo-N-cyclohexyl-N-methyl-benzylamine and its hydrochloride, m.p. 229–231° C, were prepared from 5-acetyl-2-amino-N-cyclohexyl-N-methyl-benzylamine dihydrochloride and bromine analogous to Example 11.

EXAMPLE 241

5-Acetyl-N-ethyl-2-amino-3-bromo-N-cyclohexyl-benzylamine, m.p. 111–113° C, was prepared from 5-acetyl-2-amino-N-cyclohexyl-N-ethyl-benzylamine and bromine analogous to Example 11.

EXAMPLE 242

N-(5-Acetyl-2-amino-3-bromo-benzyl)-N'-methyl-piperazine, m.p. 99–104° C, was prepared from N-(5-acetyl-2-amino-benzyl)-N'-methyl-piperazine and bromine analogous to Example 11.

EXAMPLE 243

2-Amino-3-bromo-N,N-dimethyl-5-(1-hydroxy-ethyl)-benzylamine, m.p. 69–72° C was prepared by reduction of 5-acetyl-2-amino-3-bromo-N,N-dimethyl-benzylamine with sodium borohydride analogous to Example 19.

EXAMPLE 244

2-Amino-3-bromo-N,N-diethyl-5-(1'-hydroxy-ethyl)-benzylamine, m.p. 62–65° C, was prepared by reduction of 5-acetyl-2-amino-3-bromo-N,N-diethyl-benzylamine with sodium borohydride analogous to Example 19.

EXAMPLE 245

2-Amino-3-bromo-N,N-di-n-propyl-5-(1'-hydroxy-ethyl)-benzylamine, m.p. 52–54° C, was prepared by reduction of 5-acetyl-2-amino-3-bromo-N,N-di-n-propyl-benzylamine with sodium borohydride analogous to Example 19.

EXAMPLE 246

2-Amino-3-bromo-N,N-dibutyl-5-(1'-hydroxy-ethyl)-benzylamine, m.p. 48–51° C, was prepared by reduction of 5-acetyl-2-amino-3-bromo-N,N-di-n-butyl-benzylamine, with sodium borohydride analogous to Example 19.

EXAMPLE 247

N-[2-Amino-3-bromo-5-(1'-hydroxy-ethyl)-benzyl]-pyrrolidine, m.p. 98–102° C, was prepared by reduction of N-(5-acetyl-2-amino-3-bromo-benzyl)-pyrrolidine with sodium borohydride analogous to Example 19.

EXAMPLE 248

2-Amino-3-bromo-N-cyclohexyl-N-ethyl-5-(1'-hydroxy-ethyl)-benzylamine, m.p. 117–121° C, was prepared by reduction of 5-acetyl-2-amino-3-bromo-N-cyclohexyl-N-ethyl-benzylamine with sodium borohydride analogous to Example 19.

EXAMPLE 249

N-[2-Amino-3-bromo-5-(1'-hydroxy-ethyl)-benzyl]-N'-methyl-piperazine, m.p. 134–136° C, was prepared by reduction of N-(5-acetyl-2-amino-3-bromo-benzyl)-N'-methyl-piperazine with sodium borohydride analogous to Example 19.

EXAMPLE 250

2-Amino-N-isopropyl-3-trifluoromethyl-benzylamine and its hydrochloride, m.p. 188–189° C, were prepared from 2-amino-3-trifluoromethyl-benzyl chloride and isopropylamine analogous to Example 1.

EXAMPLE 251

2-Amino-N,N-diethyl-3-trifluoromethyl-benzylamine and its hydrochloride, m.p. 194–196° C, were prepared from 2-amino-3-trifluoromethyl-benzyl chloride and diethylamine analogous to Example 1.

EXAMPLE 252

N-(2-Amino-3-trifluoromethyl-benzyl)-hexamethyleneamine and its hydrochloride, m.p. 208–209° C, were prepared from 2-amino-3-trifluoromethyl-benzyl chloride and hexamethyleneamine analogous to Example 1.

EXAMPLE 253

2-Amino-N-cyclohexyl-N-ethyl-3-trifluoromethyl-benzylamine and its hydrochloride, m.p. 189–191° C, were prepared from 2-amino-3-trifluoromethyl-benzyl chloride and N-ethyl-cyclohexylamine analogous to Example 1.

EXAMPLE 254

2-Amino-N-methyl-N-(morpholincarbonyl-methyl)-3-trifluoromethyl-benzylamine and its hydrochloride, m.p. 200–203° C (decomp.), were prepared from 2-amino-3-trifluoromethyl-benzyl chloride and sarcosine morpholide analogous to Example 1.

EXAMPLE 255

2-Amino-5-bromo-N-isopropyl-3-trifluoromethyl-benzylamine and its hydrochloride, m.p. 206–208° C, were prepared from 2-amino-N-isopropyl-3-trifluoromethyl-benzylamine and bromine analogous to Example 10.

EXAMPLE 256

2-Amino-5-bromo-N,N-diethyl-3-trifluoromethyl-benzylamine and its hydrochloride, m.p. 198–200° C, were prepared from 2-amine-N,N-diethyl-3-trifluoromethyl-benzylamine and bromine analogous to Example 10.

EXAMPLE 257

N-(2-Amino-5-bromo-3-trifluoromethyl-benzyl)-hexamethyleneamine and its hydrochloride, m.p. 223–225° C, were prepared from N-(2-amino-3-trifluoromethyl-benzyl)-hexamethyleneamine and bromine analogous to Example 10.

EXAMPLE 258

2-Amino-5-bromo-N-cyclohexyl-N-ethyl-3-trifluoromethyl-benzylamine and its hydrochloride, m.p. 204–207° C, were prepared from 2-amino-N-cyclohexyl-N-ethyl-3-trifluoromethyl-benzylamine and bromine analogous to Example 10.

EXAMPLE 259

2-Amino-5-bromo-N-methyl-N-(morpholinocarbonyl-methyl)-3-trifluoromethyl-benzylamine and its hydrochloride, m.p. 211–215° C (decomp.), were prepared from 2-amino-N-methyl-N-(morpholinocarbonyl-methyl)-3-trifluoromethyl-benzylamine and bromine analogous to Example 10.

EXAMPLE 260

2-Amino-5-chloro-N-isopropyl-3-trifluoromethyl-benzylamine and its hydrochloride, m.p. 197–200° C, were prepared from 2-amino-N-isopropyl-3-trifluoromethyl-benzylamine and iodobenzene dichloride analogous to Example 12.

EXAMPLE 261

2-Amino-5-chloro-N,N-diethyl-3-trifluoromethyl-benzylamine and its hydrochloride, m.p. 197–198° C, were prepared from 2-amino-N,N-diethyl-3-trifluoromethyl-benzylamine and iodobenzene dichloride analogous to Example 12.

EXAMPLE 262

N-(2-Amino-5-chloro-3-trifluoromethyl-benzyl)-hexamethyleneamine and its hydrochloride, m.p. 128–130° C, were prepared from N-(2-amino-3-trifluoromethyl-benzyl)-hexamethyleneamine and iodobenzene dichloride analogous to Example 12.

EXAMPLE 263

2-Amino-5-chloro-N-cyclohexyl-N-ethyl-3-trifluoromethyl-benzylamine and its hydrochloride, m.p. 202–205° C, were prepared from 2-amino-N-cyclohexyl-N-ethyl-3-trifluoromethyl-benzylamine and iodobenzene dichloride analogous to Example 12.

EXAMPLE 264

2-Amino-5-chloro-N-methyl-N-(morpholinocarbonyl-methyl)-3-trifluoromethyl-benzylamine and its hydrochloride, m.p. 200–207° C (decomp.), were prepared from 2-amino-N-methyl-N-(morpholinocarbonyl-methyl)-3-trifluoromethyl-benzylamine and iodobenzene dichloride analogous to Example 12.

EXAMPLE 265

N-(2-Amino-3-bromo-5-fluoro-benzyl)-pyrrolidine and its dihydrochloride, m.p. 173–175° C (decomp.), were prepared from 2-amino-3-bromo-5-fluoro-benzyl alcohol, thionyl-chloride and pyrrolidine analogous to Example 1.

EXAMPLE 266

2-Amino-3-bromo-5-fluoro-N-(trans-4'-hydroxy-cyclohexyl)-benzylamine and its hydrochloride, m.p. 237–239° C (decomp.), were prepared from 2-amino-3-bromo-5-fluoro-benzyl alcohol, thionylchloride and trans-4-hydroxy-cyclohexylamine analogous to Example 1.

EXAMPLE 267

2-Benzoylamino-3-bromo-5-carbethoxy-N,N-diethyl-benzylamine and its hydrochloride, m.p. 220–222° C, were prepared from 2-amino-3-bromo-5-carbethoxy-N,N-diethyl-benzylamine and benzoyl chloride in benzene analogous to Example 22.

EXAMPLE 268

3-Bromo-5-carbethoxy-2-(4'-chloro-benzoylamino)-N,N-diethyl-benzylamine and its hydrochloride, m.p. 187–193° C, were prepared from 2-amino-3-bromo-5-carbethoxy-N,N-diethyl-benzylamine and 4-chloro-benzoyl chloride in benzene analogous to Example 22.

EXAMPLE 269

2-Acetamino-5-carbomethoxy-N,N-diethylbenzylamine and its hydrochloride by method A 3.4 gm of 2-acetamino-5-carbomethoxy-benzyl bromide were dissolved in 125 ml of chloroform and after addition of 35 gm of diethylamine the mixture was allowed to stand for 15 minutes. The mixture was then evaporated to dryness in vacuo, the residue was dissolved in chloroform, the chloroform solution was extracted with dilute hydrochloric acid, and the aqueous phase was made alkaline with ammmonia and again extracted with chloroform. This chloroform extract was dried over sodium sulfate and evaporated in vacuo. The residue, consisting of the free base 2-acetamino-5-carbomethoxy-N,N-diethyl-benzylamine (m.p. 77–80° C), was converted into its hydrochloride, m.p. 213–214° C, with methanolic hydrochloric acid.

EXAMPLE 270

2-Amino-3-bromo-5-carbomethoxy-N,N-diethyl-benzylamine and its hydrochloride by method B A solution of 1.1 gm of bromine in 2 ml of acetic acid was added dropwise, while stirring at room temperature, to a solution of 1.6 gm of 2-amino-5-carbomethoxy-N,N-ethyl-benzylamine in a mixture of 27 ml of acetic acid and 3 ml of water. The mixed solution was allowed to stand for 1 hour, was then poured over ice, made alkaline with ammonia and extracted with chloroform. The chloroform extract was dried over sodium sulfate and evaporated to dryness in vacuo. The residue, 2-amino-3-bromo-5-carbomethoxy-N,N-diethyl-benzylamine, was dissolved in acetone and its hydrochloride, m.p. 180–181° C, was precipitated with ethereal hydrochloric acid.

EXAMPLE 271

2-Amino-5-carbomethoxy-N,N-diethyl-benzylamine and its hydrogen furmarate by method C A mixture of 2.5 gm of 2-acetamino-5-carbomethoxy-N,N-diethyl-benzylamine, 50 ml of methanol and 15 ml of concentrated hydrochloric acid was boiled for 30 minutes. The mixture was then poured over ice, made alkaline with ammonia, extracted with chloroform, and the chloroform extract was dried over sodium sulfate and evaporated in vacuo. The residue, 2-amino-5-carbomethoxy-N,N-diethyl-benzylamine, was converted into its hydrogen fumarate, m.p. 177–179° C, by dissolving it in methanol and adding an ethereal solution of fumaric acid.

EXAMPLE 272

2-Amino-3-bromo-5-carboxy-N-ethyl-benzylamine hdyrochloride by method E 2.7 gm of 2-amino-3-bromo-5-carbomethoxy-N-ethyl-benzylamine were boiled for 35 minutes with 65 ml of 6 N hydrochloric acid. Thereafter, upon cooling the reaction solution to −15° C, N-ethyl-2-amino-3-bromo-5-carboxy-benzylamine hydrochloride crystallized out and was recrystallized from ethanol/ether, whereupon it had a melting point of 261° C (decomp.).

EXAMPLE 273

2-Amino-5-bromo-N,N-dimethyl-3-fluoro-benzylamine and its hydrochloride by method A 5.5 gm of 2-amino-5-bromo-3-fluoro-benzyl alcohol were dissolved in 150 ml of chloroform. While stirring and cooling the solution on an ice bath. 7.13 gm (4.35 ml) of thionylchloride were added, whereby a yellow precipitate was formed. The resulting suspension was allowed to stand overnight at room temperature and was then evaporated to dryness at room temperature in a rotary evaporator. The crude substituted benzyl chloride thus obtained was suspended in 150 ml of chloroform, and 20 ml of dimethylamine were added while stirring and cooling on an ice bath, whereby a clear solution was obtained. This solution was allowed to stand for 30 minutes on an ice bath, and was then extracted twice with saturated aqueous potassium carbonate. The chloroform phase was washed with water, dried over sodium sulfate and evaporated to dryness in vacuo. The residue was taken up in absolute ethanol and acidified to pH 3 with ethereal hydrochloric acid. The precipitate formed thereby was collected by vacuum filtration and dissolved in absolute ethanol, and after addition of charcoal the solution was heated to the boiling point. After filtering off of the charcoal and addition of ether to the filtrate, the hydrochloride was obtained as colorless crystals having a melting point of 263–265° C (decomp.).

EXAMPLE 274

2-Amino-5-bromo-N-cyclohexyl-3-fluoro-N-methyl-benzylamine and its hydrochloride, m.p. 226–228° C (decomp.), were prepared from 2-amino-5-bromo-3-fluoro-benzyl alcohol, thionylchloride and N-methyl-cyclohexylamine analogous to Example 273.

EXAMPLE 275

2-Amino-5-bromo-N-(trans-4'-hydroxy-cyclohexyl)-3-fluoro-benzylamine and its hydrochloride, m.p. 231–233° C, were prepared from 2-amino-5-bromo-3-fluoro-benzyl alcohol, thionylchloride and trans-4-hydroxy-cyclohexylamine analogous to Example 273.

EXAMPLE 276

2-Amino-5-bromo-N-cyclohexyl-N-ethyl-3-fluoro-benzylamine and its hydrochloride, m.p. 193–195° C, were prepared from 2-amino-5-bromo-3-fluoro-benzyl alcohol, thionylchloride and N-ethyl-cyclohexylamine analogous to Example 273.

EXAMPLE 277

N-(2-Amino-5-carboxy-benzyl)-pyrrolidine hydrochloride, m.p. 193–194° C (decomp.), was prepared from N-(2-amino-5-carbethoxy-benzyl)-pyrrolidine and 6 N hydrochloric acid analogous to Example 272.

EXAMPLE 278

N-(2-Amino-3-bromo-5-carboxy-benzyl)-pyrrolidine hydrochloride, m.p. 267° C (decomp.), was prepared from N-(2-amino-3-bromo-5-carbethoxy-benzyl)-pyrrolidine and 6 N hydrochloric acid analogous to Example 272.

EXAMPLE 279

2-Amino-5-carboxy-N-(trans-4'-hydroxy-cyclohexyl)-benzylamine hydrochloride, m.p. 224° C (decomp.), was prepared from 2-amino-5-carbethoxy-N-(trans-4'-hydroxy-cyclohexyl)-benzylamine and 6 N hydrochloric acid analogous to Example 272.

EXAMPLE 280

2-Amino-3-bromo-5-carboxy-N-(trans-4'-hydroxy-cyclohexyl)-benzylamine hydrochloride, m.p. 279° C (decomp.) was prepared from 2-amino-3-bromo-5-carbethoxy-N-(trans-4'-hydroxy-cyclohexyl)-benzylamine and 6 N hydrochloric acid analogous to Example 272.

EXAMPLE 281

N-(2-Amino-5-carboxy-benzyl)-morpholine hydrochloride, m.p. 222° C (decomp.), was prepared from N-(2-amino-5-carbethoxy-benzyl)-morpholine and 6 N hydrochloric acid analogous to Example 272.

EXAMPLE 282

N-(2-Amino-3-bromo-5-carboxy-benzyl)-morpholine hydrochloride, m.p. 286° C (decomp.), was prepared from N-(2-amino-3-bromo-5-carbethoxy-benzyl)-morpholine and 6 N hydrochloric acid analogous to Example 272.

EXAMPLE 283

N-(2-Amino-5-carboxy-benzyl)-hexamethyleneamine dihydrochloride, m.p. >121° C (decomp.), was prepared from N-(2-amino-5-carbethoxy-benzyl)-hexamethyleneamine and 6 N hydrochloric acid analogous to Example 272.

EXAMPLE 284

N-(2-Amino-3-bromo-5-carboxy-benzyl)-hexamethyleneamine hydrochloride, m.p. >224° C (decomp.), was prepared from N-(2-amino-3-bromo-5-carbethoxy-benzyl)-hexamethyleneamine and 6 N hydrochloric acid analogous to Example 272.

EXAMPLE 285

2-Amino-5-carboxy-N-(cis-3'-hydroxy-cyclohexyl)-benzylamine dihydrochloride, m.p. 162° C (decomp.), was prepared from 2-amino-5-carbethoxy-N-(cis-3'-hydroxy-cyclohexyl)-benzylamine and 6 N hydrochloric acid analogous to Example 272.

EXAMPLE 286

2-Amino-3-bromo-5-carboxy-N-(cis-3'-hydroxy-cyclohexyl)-benzylamine hydrochloride, m.p. 119° C (decomp.), was prepared from 2-amino-3-bromo-5-carbethoxy-N-(cis-3'-hydroxy-cyclohexyl)-benzylamine and 6 N hydrochloric acid analogous to Example 272.

EXAMPLE 287

2-Acetamino-5-bromo-N,N-dimethyl-3-(dimethylamino-methyl)-benzylamine and its dihydrochloride by method A 12 gm of 4-bromo-2,6-dimethyl-acetanilide were dissolved in 1.9 liters of tetrachloromethane and the solution was heated to the boiling point. The boiling solution was irradiated with ultraviolet light, and 15.8 gm of bromine were added dropwise over a period of 50 minutes. Thereafter, the mixture was cooled to room temperature, 60 ml of dimethylamine were added, and the mixture was allowed to stand overnight, and was then extracted twice with water, dried over sodium sulfate and evaporated to dryness in vacuo. The residue was dissolved in ethanol, and the resulting solution was acidified with ethanolic hydrochloric acid. 2-Acetamino-5-bromo-N,N-dimethyl-3-(dimethylamino-methyl)-benzylamine dihydrochloride, m.p. 291° C (decomp.), crystallized out.

EXAMPLE 288

4-Bromo-2,6-bis-(pyrrolidino-methyl)-acetanilide and its dihydrochloride, m.p. 319° C (decomp.), were prepared from 4-bromo-2,6-dimethyl-acetanilide, bromine and pyrrolidine analogous to Example 287.

EXAMPLE 289

4-Bromo-2,6-bis-(piperidino-methyl)-acetanilide and its dihydrochloride, m.p. 308–312° C (decomp.), were prepared from 4-bromo-2,6-dimethyl-acetanilide, bromine and piperidine analogous to Example 287.

EXAMPLE 290

4-Bromo-2,6-bis-(morpholino-methyl)-acetanilide and its dihydrochloride, m.p. 283–284° C (decomp.), were prepared from 4-bromo-2,6-dimethyl-acetanilide, bromine and morpholine analogous to Example 287.

EXAMPLE 291

2-Amino-5-bromo-3-(dimethylamino-methyl)-N,N-dimethyl-benzylamine, and its dihydrochloride, m.p. 284–287° C (decomp.), were prepared from 2-acetamino-5-bromo-3-dimethylaminomethyl-N,N-dimethyl-benzylamine and hydrochloric acid analogous to Example 271.

EXAMPLE 292

4-Bromo-2,6-bis-(piperidino-methyl)-aniline and its dihydrochloride, m.p. 283–286° C (decomp.), were prepared from 4-bromo-2,6-bis-(piperidino-methyl)-acetanilide and hydrochloric acid analogous to Example 271.

EXAMPLE 293

4-Bromo-2,6-bis-(morpholino-methyl)-aniline and its dihydrochloride, m.p. 251–257° C (decomp.), were prepared from 4-bromo-2,6-bis-(morpholino-methyl)-acetanilide and hydrochloric acid analogous to Example 271.

EXAMPLE 294

5-Acetyl-2-amino-3-bromo-N-(trans-4'-hydroxy-cyclohexyl)-benzylamine and its hydrochloride, m.p. 214–216° C (decomp.), were prepared from 5-acetyl-2-amino-3-bromo-benzylbromide and trans-4-hydroxy-cyclohexylamine analogous to Example 269.

EXAMPLE 295

5-Acetyl-2-amino-3-chloro-N-(trans-4'-hydroxy-cyclohexyl)-benzylamine and its hydrochloride, m.p. 192–194° C (decomp.), were prepared from 4-acetamino-2-3-chloro-benzyl bromide and trans-4-hydroxy-cyclohexylamine analogous to Example 269.

EXAMPLE 296

2-Amino-5-bromo-N-[1',3'-dihydroxy-2'-methyl-propyl-(2')]-3-trifluoromethyl-benzylamine and its hydrochloride, m.p. 226–228° C (decomp.), were prepared from 2-amino-N-[1',3'-dihydroxy-2'-methyl-propyl-(2')]-3-trifluoromethyl-benzylamine and bromine analogous to Example 270.

EXAMPLE 297

2-Amino-N-[1',3'-dihydroxy-2'-methyl-propyl-(2')]-3-trifluoromethyl-benzylamine, m.p. 110–112° C, was prepared from 2-amino-3-trifluoromethyl-benzyl chloride and 2-amino-2-methy-1,3-propandiol analogous to Example 269.

EXAMPLE 298

2-Amino-5-bromo-N-(cis-3'-hydroxy-cyclohexyl)-3-trifluoromethyl-benzylamine and its hydrochloride, m.p. >70° C (decomp.), were prepared from 2-amino-N-(cis-3'-hydroxy-cyclohexyl)-3-trifluoromethyl-benzylamine and bromine analogous to Example 270.

EXAMPLE 299

2-Amino-N-(cis-3'-hydroxy-cyclohexyl)-3-trifluoromethyl-benzylamine and its hydrochloride, m.p.

196–200° C, were prepared from 2-amino-3-trifluoromethyl-benzyl chloride and cis-3-hydroxycyclohexylamine analogous to Example 269.

EXAMPLE 300

2-Amino-5-bromo-N-(hydroxy-tert.butyl)-3-trifluoromethyl-benzylamine and its hydrochloride, m.p. 226–228° C (decomp.), were prepared from 2-amino-N-(hydroxy-tert.butyl)-3-trifluoromethyl-benzylamine and bromine analogous to Example 270.

EXAMPLE 301

2-Amino-5-bromo-N-(trans-4'-hydroxy-cyclohexyl)-3-trifluoromethyl-benzylamine and its hydrochloride, m.p. 233–236° C decomp.), were prepared from 2-amino-N-(trans-4'-hydroxy-cyclohexyl)-3-trifluoromethyl-benzylamine and bromine analogous to Example 270.

EXAMPLE 302

2-Amino-N-(trans-4'-hydroxy-cyclohexyl)-3-trifluoromethyl-benzylamine and its hydrochloride, m.p. 228–230° C (decomp.), were prepared from 2-amino-3-trifluoromethyl-benzyl chloride and trans-4-hydroxycyclohexylamine analogous to Example 269.

EXAMPLE 303

2-Amino-N-(hydroxy-tert.butyl)-3-trifluoromethyl-benzylamine, m.p. 110–112° C, was prepared from 2-amino-3-trifluoromethyl-benzyl chloride and hydroxy-tert.butylamine analogous to Example 269.

EXAMPLE 304

2-Amino-5-chloro-N,N-dimethyl-3-trifluoromethyl-benzylamine and its hydrochloride, m.p. 210–212° C (decomp.), were prepared from 2-amino-3-trifluoromethyl-benzylamine and iodobenzene dichloride analogous to Example 270.

EXAMPLE 305

2-Amino-5-bromo-N,N-dimethyl-3-trifluoromethyl-benzylamine and its hydrochloride, m.p. 184–185° C, were prepared from 2-amino-N,N-dimethyl-3-trifluoromethyl-benzylamine and bromine analogous to Example 270.

EXAMPLE 306

2-Amino-5-carbethoxy-N-ethyl-benzylamine and its hydrochloride by method C 3.8 gm of 2-amino-N-benzyl-5-carbethoxy-N-ethyl-benzylamine were hydrogenated in a mixture of 50 ml of methanol and 1 ml of concentrated hydrochloric acid at room temperature and at a hydrogen pressure of 5 atmospheres in the presence of palladized charcoal. Then, the catalyst was filtered off, and the filtrate was evaporated to dryness in vacuo. The residue was recrystallized from ethanol by addition of ether, yielding 2-amino-5-carbethoxy-N-ethyl-benzylamine hydrochloride, m.p. 173–176° C (decomp.).

EXAMPLE 307

3-Bromo-2-butyrylamino-5-carbethoxy-N,N-diethyl-benzylamine and its hydrochloride 3 gm of 2-Amino-3-bromo-5-carbethoxy-N,N-diethyl-benzylamine were dissolved in 30 ml of benzene, and the solution was heated for 30 minutes with 3 ml of butyric acid chloride at 50° C. Thereafter, the mixture was evaporated to dryness in vacuo, and the residue was purified by chromatography on silicagel (eluant: benzene/ethyl acetate = 6:1), yielding 3-bromo-2-butyrylamino-5-carbethoxy-N,N-diethyl-benzylamine, which was converted into its hydrochloride, m.p. 134° C, with ethanolic hydrochloric acid.

EXAMPLE 308

2-Amino-N-benzyl-5-carbethoxy-N-ethyl-benzylamine and its hydrochloride, m.p. >61° C (decomp.), were prepared from 2-acetamino-5-carbethoxy-benzyl bromide and N-ethyl-benzylamine analogous to Example 269, followed by hydrolysis of the crude 2-acetamino-N-ethyl-N-benzyl-5-carbethoxy-benzylamine thus obtained with ethanol/hydrochloric acid analogous to Example 271.

EXAMPLE 309

N-(2-Acetamino-5-carbethoxy-benzyl)-pyrrolidine, a chromatographically homogeneous oil, was prepared from 2-acetamino-5-carbethoxy-benzyl bromide and pyrrolidine analogous to Example 269.

EXAMPLE 310

N-(2-Amino-5-carbethoxy-benzyl)-pyrrolidine and its dihydrochloride, m.p. 146–149° C, were prepared from N-(2-acetamino-5-carbethoxy-benzyl)-pyrrolidine and ethanol/hydrochloric acid analogous to Example 271.

EXAMPLE 311

N-(2-Amino-3-bromo-5-carbethoxy-benzyl)-pyrrolidine and its hydrochloride, m.p. 204–205° C, were prepared from N-(2-amino-5-carbethoxy-benzyl)-pyrrolidine and bromine analogous to Example 270.

EXAMPLE 312

2-Amino-5-carbethoxy-N-(trans-4'-hydroxy-cyclohexyl)-benzylamine and its hydrochloride, m.p. 237° C (decomp.), were prepared from 2-acetamino-5-carbethoxy-benzyl bromide and trans-4-hydroxycyclohexylamine analogous to Example 269, followed by hydrolysis of the 2-acetamino-5-carbethoxy-N-(trans-4'-hydroxy-cyclohexyl)-benzylamine thus obtained with ethanol/hydrochloric acid analogous to Example 271.

EXAMPLE 313

2-Amino-3-bromo-5-carbethoxy-N-(trans-4'-hydroxy-cyclohexyl)-benzylamine and its hydrochloride, m.p. 137° C (decomp.), were prepared from 2-amino-5-carbethoxy-N-(trans-4'-hydroxy-cyclohexyl)-benzylamine and bromine analogous to Example 270.

EXAMPLE 314

2-Acetamino-3-bromo-5-carbethoxy-N-cyclohexyl-N-methyl-benzylamine and its hydrochloride, m.p. 220–223° C, were prepared from 2-amino-3-bromo-5-carbethoxy-N-cyclohexyl-N-methyl-benzylamine and acetyl chloride analogous to Example 307.

EXAMPLE 315

N-(2-Amino-5-carbethoxy-benzyl)-morpholine and its hydrochloride, m.p. 205° C (decomp.), were prepared from 2-acetamino-5-carbethoxy-benzyl bromide and morpholine analogous to Example 269, followed by hydrolysis of the N-(2-acetamino-5-carbethoxy-benzyl)-morpholine thus obtained with ethanol/hydrochloric acid analogous to Example 271.

EXAMPLE 316

N-(2-Amino-3-bromo-5-carbethoxy-benzyl)-morpholine and its hydrochloride, m.p. 221° C (decomp.), were prepared from N-(2-amino-5-carbethoxy-benzyl)-morpholine and bromine analogous to Example 270.

EXAMPLE 317

N-(2-Amino-5-carbethoxy-benzyl)-hexamethyleneamine and its hydrochloride, m.p. 168–169° C, were prepared from N-(2-acetamino-5-carbethoxy-benzyl)-hexamethyleneamine and ethanol/hydrochloric acid analogous to Example 271.

EXAMPLE 318

N-(2-Amino-3-bromo-5-carbethoxy-benzyl)-hexamethyleneamine and its hydrochloride, m.p. 219–221° C, were prepared from N-(2-amino-5-carbethoxy-benzyl)-hexamethyleneamine and bromine analogous to Example 270.

EXAMPLE 319

2-Acetamino-N-benzyl-5-carbethoxy-N-tert.butyl-benzylamine and its hydrochloride, m.p. 208° C (decomp.), were prepared from 2-acetamino-5-carbethoxy-benzyl bromide and N-tert.butyl-benzylamine analogous to Example 269.

EXAMPLE 320

2-Amino-5-carbethoxy-N-(cis-3'-hydroxy-cyclohexyl)-benzylamine and its hydrochloride, m.p. 201–203° C, were prepared from 2-acetamino-5-carbethoxy-benzyl bromide and cis-3-hydroxy-cyclohexylamine analogous to Example 269, followed by hydrolysis of the 2-acetamino-5-carbethoxy-N-(cis-3-hydroxy-cyclohexyl)benzylamine thus obtained with ethanol/hydrochloric acid analogous to Example 271.

EXAMPLE 321

2-Amino-3-bromo-5-carbethoxy-N-(cis-3'-hydroxy-cyclohexyl)benzylamine and its hydrochloride, m.p. 103° C. (decomp.), were prepared from 2-amino-5-carbethoxy-N-(cis-3-hydroxy-cyclohexyl)-benzylamine and bromine analogous to Example 270.

EXAMPLE 322

2-Amino-5-carbomethoxy-N-(trans-4'-hydroxy-cyclohexyl)-benzylamine and its fumarate, m.p. 221° C (decomp.), were prepared from 2-acetamino-5-carbomethoxy-benzyl bromide and trans-4-hydroxy-cyclohexylamine analogous to Example 269, followed by hydrolysis of the 2-acetamino-5-carbomethoxy-N-(trans-4'-hydroxy-cyclohexyl)-benzylamine thus obtained with methanol/hydrochloric acid analogous to Example 271.

EXAMPLE 323

2-Amino-N,N-diethyl-5-(isopropoxy-carbonyl)-benzylamine and its hydrogen fumarate, m.p. 158° C, were prepared from 2-acetamino-5-(isopropoxy-carbonyl)-benzyl bromide and diethylamine analogous to Example 269, followed by hydrolysis of the 2-acetamino-N,N-diethyl-5-(isopropoxy-carbonyl)-benzylamine thus obtained with isopropanol/hydrochloric acid analogous to Example 271.

EXAMPLE 324

2-Acetamino-N-benzyl-5,N-dimethyl-benzylamine, an oil, was prepared from 2-acetamino-5-methyl-benzyl bromide and N-methyl-benzylamine analogous to Example 269; proof of structure by UV-, NMR- and IR-spectra.

EXAMPLE 325

N-Ethyl-2-amino-3-bromo-5-carbethoxy-benzylamine, m.p. 199–201° C, was prepared from N-ethyl-2-amino-5-carbethoxy-benzylamine and bromine analogous to Example 270.

EXAMPLE 326

4-Bromo-2,6-bis-(pyrrolidino-methyl)-aniline and its dihydrochloride, m.p. 274–276° C (decomp.), were prepared from 4-bromo-2,6-bis-(pyrrolidino-methyl)-acetanilide and hydrochloric acid analogous to Example 271.

EXAMPLE 327

2-Amino-3-bromo-N-(trans-4'-hydroxy-cyclohexyl)-5-methoxybenzylamine, an amorphous substance, was prepared from 2-amino-3-bromo-5-methoxy-benzyl alcohol, thionylchloride and trans-4-hydroxy-cyclohexylamine analogous to Example 273; proof of structure by IR-, UV- and NMR-spectra.

EXAMPLE 328

2-Amino-3-carboxy-N-cyclohexyl-N-ethyl-benzylamine and its hydrochloride, m.p. 193–197° C, were prepared from 2-amino-3-carboxy-benzyl bromide and N-ethyl-cyclohexylamine analogous to Example 25.

EXAMPLE 329

2-Amino-5-bromo-3-carboxy-N-cyclohexyl-N-ethyl-benzylamine and its hydrochloride, m.p. 130–140° C, were prepared from 2-amino-5-bromo-3-carboxy-benzyl bromide and N-ethyl-cyclohexylamine analogous to Example 25.

The compounds of the present invention, that is those embraced by formula I above and their non-toxic pharmacologically acceptable acid addition salts, have useful pharmacodynamic properties. More particularly, the compounds of this invention exhibit anti-ulcerogenic, secretolytic and antitussive activities, as well as a stimulating effect upon the surfactant or antiatelectasis factor of the alveoli in warm-blooded animals, such as guinea pigs, rabbits, rats and cats.

The above-indicated pharmacological activities were ascertained for the compounds of the present invention by the methods described below, and the following are illustrative results obtained for a representative number of compounds, where A = 2-amino-3-bromo-5-carbethoxy-N,N-diethyl-benzylamine hydrochloride, B = 2-amino-3-bromo-5-carboxy-N-cyclohexyl-N-ethyl-benzylamine hydrochloride, C = 2-amino-3-bromo-N-cyclohexyl-N-ethyl-3-fluoro-benzylamine hydrochloride, D = N-(2-amino-5-bromo-3-methyl-benzyl)-hexamethyleneamine dihydrochloride, E = N-(2-amino-5-bromo-4-tert.butyl-benzyl)-morpholine dihydrochloride, F = 5-acetyl-2-amino-3-bromo-N,N-dimethyl-benzylamine and G = 2-amino-3-bromo-N,N-dimethyl-5-fluoro-benzylamine hydrochloride.

(1) Secretolytic Effect

The expectorant activity was tested on anesthetized rabbits and guinea pigs after oral application of 8 mgm/kg of the test compound to 6–8 animals. The increase in secretion within 2 hours was calculated from the amounts of secretion before and after application of the substance [see Perry and Boyd in Pharmakol. exp. Therap. 73, 65 (1941)].

The circulatory effect in cats was determined under chloralose-urethane anesthesia after intravenous application of 2,4 and 8 mgm/kg of the test compound (3 animals per dose).

| Tests in guineapigs: | | |
|---|---|---|
| Compound | Increase in secretion | Circulatory effect |
| A | + 90% | 2,4 and 8 mgm/kg:no change |
| B | + 81% | 2,4 and 8 mgm/kg:no change |
| C | + 100% | |
| G | + 84% | |
| Tests in rabbits: | | |
| Compound | Increase in secretion | |
| D | + 72% | |
| E | + 77% | |
| F | + 75% | |

(2) Anti-ulcerogenic activity

The inhibiting effect of the test compounds on the formation of ulcers was determined according to the method of K.Takagi et al [Jap. J. Pharmac, 19, 418 (1969)]. The abdominal cavity of anesthetized female rats having a body weight from 220 to 250 gm was opened and the stomach was exposed. Then, 0.05 ml of an aqueous 5% acetic acid solution was injected between the muscularis mucosae and submucosa of the stomach. Thereafter, the abdominal cavity was closed again. The ulcers formed in the mucosa after 3 to 5 days were treated for three weeks by admixing the test compound in question with the food at dosage levels of 50 and 100 mgm/kg (6 animals/dose). The control animals were fed with the pulverized food only.

After treatment for three weeks the animals were killed, the stomach was removed, and the size of the ulcers was determined by measurement of their length and width. The anti-ulcerogenic activity of the test compound was determined by the size of the ulcers comparing with the control values (100%):

A peroral dosage of 50 mgm/kg of compound A produced a 52% reduction of the ulcers, and a peroral dosage of 100 mgm/kg produced a 79% reduction of the ulcers, compared with control values.

(3) Acute toxicity:

The acute toxicity of the test compounds was determined after a single application of 1000 or 2000 mgm/kg p.o., respectively, to 5 white mice each.

| Compound | Acute toxicity |
|---|---|
| A | >2000 mgm/kg p.o. (0 out of 5 animals died) |
| B | >1000 mgm/kg p.o. (0 out of 5 animals died) |
| C | >1000 mgm/kg p.o. (0 out of 5 animals died) |
| D | >1000 mgm/kg p.o. (0 out of 5 animals died) |
| E | >1000 mgm/kg p.o. (0 out of 5 animals died) |
| F | ~1000 mgm/kg p.o. (2 out of 5 animals died) |
| G | >1000 mgm/kg p.o. (0 out of 5 animals died) |

For pharmaceutical purposes the compounds according to the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like.

The single effective dose is from 0.016 to 1.67 mgm/kg, preferably 0.066 to 1.0 mgm/kg body weight. The daily dose rate is 0.032 to 5.0 mgm/kg, preferably 0.064 to 3.3 mgm/kg body weight.

The following examples illustrate a few pharmaceutical compositions comprising a compound of the present invention as an active ingredient and represent the best modes contemplated of putting the invention to practical use. The parts are parts by weight unless otherwise specified.

EXAMPLE 330

Syrup

The syrup was compounded from the following ingredients:

| | | | |
|---|---|---|---|
| 2-Amino-3-bromo-5-carbethoxy-N,N-diethyl-benzylamine hydrochloride | | 0.04 | parts by vol. |
| Tartaric acid | | 0.50 | " |
| Benzoic acid | | 0.20 | " |
| Ammonium chloride | | 0.40 | " |
| Glycerin | | 10.00 | " |
| Sorbitol | | 50.00 | " |
| Red food color | | 0.01 | " |
| Flavoring | | 0.25 | " |
| Ethanol | | 10.00 | " |
| Distilled water | q.s.ad | 100.00 | " |

Preparation:

45 gm of the distilled water was warmed to 80° C. Then the tartaric acid, the benzoic acid, the benzylamine, the naphthol and the sorbitol were successively dissolved in the water which was subsequently mixed with the glycerin and an aqueous 20% solution of ammonium chloride. After cooling to room temperature, the ethanol and the flavoring were stirred into the mixture. The syrup was diluted to the indicated volume with distilled water and filtered. Each 10 ml portion of the syrup contained 4 mgm of the benzylamine hydrochloride, and was an oral dosage unit composition with very effective secretolytic, anti-ulcerogenic and antitussive action, as well as a stimulant effect upon the production of the surfactant or antiatelectasis factor of the alveoli.

EXAMPLE 331

Drop Solution

The solution was compounded from the following ingredients:

| | | | |
|---|---|---|---|
| 2-Amino-3-bromo-5-carbethoxy-N,N-diethyl-benzylamine hydrochloride | | 0.40 | parts by vol. |
| p-Hydroxy-benzoic acid methyl ester | | 0.07 | " |
| p-Hydroxy-benzoic acid propyl ester | | 0.03 | " |
| Polyvinylpyrrolidone | | 5.00 | " |
| Anise oil | | 0.01 | " |
| Fennel oil | | 0.001 | " |
| Ethanol | | 10.00 | " |
| Distilled water | q.s.ad | 100.00 | " |

Preparation:

The p-hydroxy-benzoic acid esters, the polyvinylpyrrolidone and the benzylamine salt were successively dissolved in the distilled water warmed to 80° C. The solution was cooled and subsequently mixed with the mixture of the aromatic oils and the ethanol. The solution was diluted to the indicated volume with distilled water and filtered. Each ml of drop solution contained 4 mgm of the benzylamine hydrochloride, and was an oral dosage unit composition with very effective secretolytic, anti-ulcerogenic and antitussive action, as well as a stimulant effect upon the production of the surfactant or antiatelectasis factor of the alveoli.

EXAMPLE 332

Tablets

The tablet composition was compounded from the following ingredients:

| | | |
|---|---|---|
| 2-Amino-3-bromo-5-carbethoxy-N,N-diethyl-benzylamine hydrochloride | 4.0 | parts |
| Lactose | 60.0 | parts |
| Potato starch | 41.0 | parts |
| Polyvinylpyrrolidone | 4.0 | parts |
| Magnesium stearate | 1.0 | parts |
| Total | 110.0 | parts |

Preparation:

The benzylamine salt was admixed with the lactose and the potato starch and granulated through a screen of 1 mm mesh-size with an aqueous 20% solution of the polyvinylpyrrolidone. The moist granulate was dried at 40° C, again passed through the above mentioned screen and admixed with the magnesium stearate. The mixture was compressed into 110 mgm-tablets. Each tablet contained 4 mgm of the benzylamine salt and was an oral dosage unit composition with very effective secretolytic, anti-ulcerogenic and antitussive action, as well as a stimulant action upon the production of the surfactant or antiatelectasis factor of the alveoli.

EXAMPLE 333

Coated Pills

The pill core composition was compounded from the following ingredients:

| | | |
|---|---|---|
| 2-Amino-3-bromo-5-carbethoxy-N,N-diethyl-benzylamine hydrochloride | 4.0 | parts |
| Lactose | 60.0 | parts |
| Potato starch | 41.0 | parts |
| Polyvinylpyrrolidone | 4.0 | parts |
| Magnesium stearate | 1.0 | parts |
| Total | 110.0 | Parts |

Preparation:

The benzylamine salt was admixed with the lactose and the potato starch and granulated through a screen of 1 mm mesh-size with an aqueous 20% solution of the polyvinylpyrrolidone. The moist granulate was dried at 40° C, again passed through the above mentioned screen and admixed with the magnesium stearate. The mixture was compressed into 110 mgm-pill cores, which were coated in conventional manner with a thin shell consisting essentially of a mixture of sugar and talcum, and were then polished with beeswax. Each coated pill contained 4 mgm of the benzylamine salt and was an oral dosage unit composition with very effective secretolytic, anti-ulcerogenic and antitussive action, as well as a stimulant effect upon the production of the surfactant or antiatelectasis factor of the alveoli.

EXAMPLE 334

Suppositories

The suppository composition was compounded from the following ingredients:

| | | |
|---|---|---|
| 1-Amino-3-bromo-5-carbethoxy-N,N-diethyl-benzylamine hydrochloride | 4.0 | parts |
| Suppository base (e.g. cocoa butter) | 1696.0 | parts |
| Total | 1700.0 | parts |

Preparation:

The finely pulverized benzylamine salt was stirred into the molten suppository base which had been cooled to 40° C, and the mixture was homogenized. 1700 mgm-portions of the mixture were then poured at about 35° C into cooled suppository molds and allowed to harden therein. Each suppository contained 4 mgm of the benzylamine salt and was a rectal dosage unit composition with very effective secretolytic, anti-ulcerogenic and antitussive action, as well as a stimulant effect upon the production of the surfactant or antiatelectasis factor of the alveoli.

EXAMPLE 335

Hypodermic solution

The solution was compounded from the following ingredients:

| | | | |
|---|---|---|---|
| 2-Amino-3-bromo-5-carboxy-N-ethyl-N-cyclohexyl-benzylamine hydrochloride | | 4.0 | parts by vol. |
| Tartaric acid | | 2.0 | " |
| Glucose | | 95.0 | " |
| Distilled water | q.s.ad | 2000.0 | " |

Preparation:

Some of the distilled water was warmed to 80° C, and the tartaric acid and the benzylamine salt were dissolved therein while stirring. After cooling to room temperature, the glucose was dissolved therein, the solution was filtered until free from suspended matter, and the filtrate was filled into white 2 ml-ampules under aseptic conditions. The filled ampules were then sealed and sterilized at 120° C for 20 minutes. Each ampule contained 4 mgm of the benzylamine salt and was an injectable parenteral dosage unit composition with very effective secretolytic, anti-ulcerogenic and antitussive action, as well as a stimulant effect upon the production of the surfactant or antiatelectrasis factor of the alveoli.

Analogous results were obtained when any one of the other compounds embraced by formula I or a non-toxic acid addition salt thereof was substituted for the particular benzylamine salt in Examples 330 through 335. Likewise, the amount of active ingredient in these illustrative examples may be varied to achieve the concentration ranges set forth above and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

[1. A compound of the formula

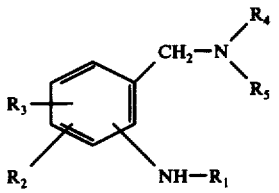

wherein $R_1$ is hydrogen, lower alkanoyl, benzoyl or halobenzoyl, $R_2$ is hydrogen, chlorine or bromine, $R_3$ is carboxyl or lower carbalkoxy, and $R_4$ and $R_5$ are each hydrogen, alkyl of 1 to 5 carbon atoms, mono- or di-hydroxy(alkyl of 1 to 5 carbon atoms), alkenyl of 2 to 4 carbon atoms, cycloalkyl of 5 to 7 carbon atoms, mono- or dihydroxy(cycloalkyl of 5 to 7 carbon atoms) or benzyl, provided, however, that when $R_3$ is carboxyl, $R_1$, $R_2$, $R_4$ and $R_5$ are other than all hydrogen at the same time, or a non-toxic, pharmacologically acceptable acid addition salt thereof.]

2. A compound of claim [1]*4*, which is 2-amino-3-bromo-5-carbethoxy-N,N-diethyl-benzylamine or a non-toxic, pharmacologically acceptable acid addition salt thereof.

3. A compound of claim [1]*4*, which is 2-amino-3-bromo-5-carboxy-N-cyclohexyl-N-ethyl-benzylamine or a non-toxic, pharmacologically acceptable acid addition salt thereof.

*4. A compound of the formula*

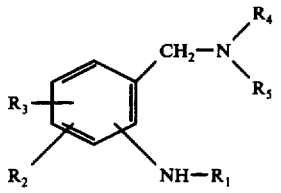

*wherein*

*$R_1$ is hydrogen, lower alkanoyl, benzoyl or halobenzoyl;*
*$R_2$ is chlorine or bromine;*
*$R_3$ is carboxyl or lower carbalkoxy; and*
*$R_4$ and $R_5$ are each hydrogen, alkyl of 1 to 5 carbon atoms, mono- or di-hydroxy(alkyl of 1 to 5 carbon atoms), alkenyl of 2 to 4 carbon atoms, cycloalkyl of 5 to 7 carbon atoms, mono- or di-hydroxy(cycloalkyl of 5 to 7 carbon atoms) or benzyl;*

*or a non-toxic, pharmacologically acceptable acid addition salt thereof.*

*5. A compound according to claim 4,*

*where*

*$R_1$ is hydrogen, lower alkanoyl, benzoyl or halobenzoyl;*
*$R_2$ is chlorine or bromine;*
*$R_3$ is carboxyl or lower carbalkoxy; and*
*$R_4$ and $R_5$ are each alkyl of 1 to 5 carbon atoms, mono- or di-hydroxy(alkyl of 1 to 5 carbon atoms), alkenyl of 2 to 4 carbon atoms, cycloalkyl of 5 to 7 carbon atoms, mono- or di-hydroxy(cycloalkyl of 5 to 7 carbon atoms) or benzyl;*

*or a non-toxic, pharmacologically acceptable acid addition salt thereof.*

*6. A compound of claim 4,*

*where*

*$R_1$ is hydrogen;*
*$R_2$ is chlorine or bromine;*
*$R_3$ is carboxyl or lower carbalkoxy; and*
*$R_4$ and $R_5$ are each alkyl of 1 to 5 carbon atoms or cycloalkyl of 5 to 7 carbon atoms;*

*or a non-toxic, pharmacologically acceptable acid addition salt thereof.*

* * * * *

UNITED STATES PATENT OFFICE

CERTIFICATE OF CORRECTION

Patent No. RE 29,628 Dated May 9, 1978

Inventor(s) JOHANNES KECK, KLAUS-REINHOLD NOLL, HELMUT PIEPER, GERD KRÜGER and SIGFRID PÜSCHMANN It is certified that error appears in the above-identified patent and that said Letters Patent are hereby corrected as shown below:

Col. 2, lines 18 and 19, after "above" insert --with an amine of the formula--.

Col. 5, line 30, delete "control".

Col. 14, line 22, "make" should be --made--.

Col. 16, line 13, after "acetamino-" insert --N-ethyl- --.

Col. 17, line 11, "1-amino-" should be --2-amino- --.

Col 27, line 49, after "Amino-3-" insert --bromo--.

Col. 28, line 12, after "201°" insert --C.--.

Col. 31, lines 23-25, delete "m.p. 118-119°C, was prepared by hydrolysis of 2-acetamino-5-bromo-N,3-dimethyl-N-(cis-3'-hydroxy-cyclohexyl)-benzylamine".

Col. 36, line 25, "ethanol" should be --ethanolic--;

line 67, "ethanol" should be --ethanolic--.

UNITED STATES PATENT OFFICE
CERTIFICATE OF CORRECTION

Patent No. RE 29,628 Dated May 9, 1978

Inventor(s) JOHANNES KECK, KLAUS-REINHOLD NOLL, HELMUT PIEPER, GERD KRÜGER and SIGFRID PÜSCHMANN It is certified that error appears in the above-identified patent and that said Letters Patent are hereby corrected as shown below:

Col. 39, line 33, "amine" should be --amino--.

Col. 41, line 13, "ethyl" should be --diethyl--;

line 26, "furmarate" should be --fumarate--.

Col. 44, line 41, after "acetamino-2-" insert --amino--.

Col. 52, line 49, "antiatelectrasis" should be --antiatelectasis--.

Signed and Sealed this

Thirty-first Day of October 1978

[SEAL]

Attest:

RUTH C. MASON
Attesting Officer

DONALD W. BANNER
Commissioner of Patents and Trademarks